United States Patent
Nishi et al.

(10) Patent No.: US 7,709,235 B2
(45) Date of Patent: May 4, 2010

(54) 5-SUBSTITUTED HYDANTOIN RACEMASE, DNA ENCODING THE SAME, RECOMBINANT DNA, TRANSFORMED CELL, AND PROCESS FOR PRODUCTION OF OPTICALLY ACTIVE N-CARBAMYLAMINO ACID OR OPTICALLY ACTIVE AMINO ACID

(75) Inventors: Kenichi Nishi, Takasago (JP); Satohiro Yanagisawa, Takasago (JP); Hirokazu Nanba, Takasago (JP); Makoto Ueda, Takasago (JP); Naoto Noro, Takasago (JP)

(73) Assignee: Kaneka Corporation, Osaka (JP)

( * ) Notice: Subject to any disclaimer, the term of this patent is extended or adjusted under 35 U.S.C. 154(b) by 185 days.

(21) Appl. No.: 11/883,306

(22) PCT Filed: Jan. 26, 2006

(86) PCT No.: PCT/JP2006/301253

§ 371 (c)(1),
(2), (4) Date: Jul. 30, 2007

(87) PCT Pub. No.: WO2006/080409

PCT Pub. Date: Aug. 3, 2006

(65) Prior Publication Data

US 2008/0261268 A1    Oct. 23, 2008

(30) Foreign Application Priority Data

Jan. 31, 2005    (JP) .............................. 2005-022802

(51) Int. Cl.
| | |
|---|---|
| C12P 21/06 | (2006.01) |
| C12P 13/04 | (2006.01) |
| C12P 17/10 | (2006.01) |
| C12N 9/00 | (2006.01) |
| C12N 1/20 | (2006.01) |
| C07H 21/04 | (2006.01) |

(52) U.S. Cl. ...................... 435/106; 435/69.1; 435/121; 435/183; 435/233; 435/252.3; 536/23.2

(58) Field of Classification Search ........................ None
See application file for complete search history.

(56) References Cited

U.S. PATENT DOCUMENTS

2002/0102713 A1    8/2002    Suzuki et al.
2005/0084946 A1    4/2005    Suzuki et al.
2006/0246553 A1    11/2006    Suzuki et al.

FOREIGN PATENT DOCUMENTS

| JP | 61-047194 A | 7/1986 |
|---|---|---|
| JP | 62-122591 A | 6/1987 |
| JP | 4-271784 A | 9/1992 |
| JP | 2003-210176 A | 7/2003 |
| JP | 2003-210177 A | 7/2003 |
| WO | WO 03/100050 A1 | 12/2003 |

OTHER PUBLICATIONS

Accession AAR28042, published Mar. 18, 1993.*
Chica et al. Curr Opin Biotechnol. Aug. 2005;16(4):378-84.*
Sen et al. Appl Biochem Biotechnol. Dec. 2007;143(3):212-23.*
Ken Watabe et al., "Identification and Sequencing of a Gene Encoding a Hydantoin Racemase from the Native Plasmid of Pseudomonas sp. Strain NS671", J. Bacteriol., 1992, p. 3461-3466, vol. 174, No. 11.
Weise, et al., "Hydantoin racemase from *Arthrobacter aurescens* DSM 3747: heterologous expression, purification and characterization," *J. Biotech. 80*:217-230 (2000).
Watabe, et al., "Purification and Characterization of the Hydantoin Racemase of *Pseudomonas* sp. Strain NS671 Expressed in *Escherichia coli*," *J. Bacteriol. 174*(24):7989-7995 (1992).
Hils, et al., "Cloning and characterization of genes from *Agrobacterium* sp. IP I-671 involved in hydantoin degradation," *Appl. Microbiol. Biotechnol. 57*:680-688 (2001).
Martinez-Rodriquez, et al., "Complete Conversion of D,L-5-Monosubstituted Hydantoins with a Low Velocity of Chemical Racemization into D-Amino Acids Using Whole Cells of Recombinant *Escherichia coli*," *Biotechnol. Prog. 18*:1201-1206 (2002).
Martinez-Rodriquez, et al., "Molecular Cloning, Purification, and Biochemical Characterization of Hydantoin Racemase from the Legume Symbiont *Sinorhizobium meliloti* CECT 4114," *Appl. Environ. Microbiol. 70*(1):625-630 (2004).

* cited by examiner

*Primary Examiner*—Christian L Fronda
(74) *Attorney, Agent, or Firm*—Sughrue Mion, PLLC

(57) ABSTRACT

Disclosed are a novel hydantoin racemase and a process for producing an optically active N-carbamylamino acid or an optically active amino acid using the hydantoin racemase. A novel hydantoin racemase isolated and purified from *Bacillus* sp. Strain KNK519HR; a gene encoding the hydantoin racemase; a recombinant plasmid having the gene introduced therein; a transformant having the hydantoin racemase gene introduced therein; and a process for producing an optically active N-carbamylamino acid or an optically active amino acid characterized in that a 5-substituted hydantoin compound is treated in the presence of hydantoinase and N-carbamylamino acid amidohydrolase as well as the hydantoin racemase.

20 Claims, 4 Drawing Sheets

```
                        SEQUENCE LISTING

<160> NUMBER OF SEQ ID NOS: 12

<210> SEQ ID NO 1
    <211> LENGTH: 249
    <212> TYPE: PRT
    <213> ORGANISM: Bacillus sp.

<400> SEQUENCE: 1

Met Lys Ile Lys Val Ile Asn Pro Asn Thr Thr Leu Ala Met Thr Lys
    1               5                   10                  15

Gly Ile Glu His Ala Ala Lys Ser Ala Ala Arg Ser Asp Thr Gln Ile
                20                  25                  30

Val Ala Val Ser Pro Lys Met Gly Pro Ala Ser Ile Glu Ser Tyr Tyr
                35                  40                  45

Asp Glu Tyr Leu Ser Ile Pro Gly Val Ile Glu Glu Ile Lys Lys Gly
            50                  55                  60

Glu Glu Glu Gly Val Asp Ala Phe Val Ile Ala Cys Trp Gly Asp Pro
    65                  70                  75                  80

Gly Leu His Ala Ala Arg Glu Val Thr Asp Lys Pro Val Val Gly Ile
                    85                  90                  95

Ala Glu Ser Ser Val Tyr Leu Ala Ser Met Leu Ala Ala Arg Phe Ser
                    100                 105                 110

Val Val Thr Val Leu Pro Arg Ile Lys Thr Met Leu Glu Asp Leu Val
                    115                 120                 125

Asp Ser Tyr Gly Met Gln Lys Arg Val Val Asn Ile Arg Thr Thr Pro
                130                 135                 140

Met Gly Val Leu Asp Phe Glu Arg Asp Pro Glu Ala Gly Ile Glu Met
    145                 150                 155                 160

Leu Arg Gln Glu Gly Lys Arg Ala Val Glu Glu Asp Asn Ala Glu Ala
                    165                 170                 175

Ile Leu Leu Gly Cys Ala Gly Met Ala Glu Phe Ala Asp Ser Leu Glu
                    180                 185                 190

Lys Glu Leu Gly Val Pro Val Ile Asp Gly Val Val Ala Gly Val Lys
                    195                 200                 205

Phe Ala Glu Ala Ile Val Asp Leu Gly Lys Lys Thr Ser Lys Leu Lys
                    210                 215                 220
```

```
Thr Tyr Lys Tyr Pro Glu Lys Glu Tyr Val Gly Ala Leu Glu Asn
225                 230                 235                 240

Phe Gly Leu Asn Gln Thr Thr Thr Lys
                245
```

<210> SEQ ID NO 2
<211> LENGTH: 750
<212> TYPE: DNA
<213> ORGANISM: Bacillus sp.

<400> SEQUENCE: 2

```
atgaaaatta aagttatcaa cccgaataca actttggcaa tgacaaaggg aattgaacat    60
gctgctaagt cagctgcaag atctgatact caaattgttg cagtgagtcc taaatgggt   120 ccggcttcaa ttgaatccta ctatgatgaa tatttaagta ttccaggagt aattgaggaa   180
attaaaaagg gagaagaaga aggagtagat gcatttgtta tagcatgctg gggagaccct   240
ggattacatg ctgcgagaga agtaacagat aaaccagttg taggcattgc ggaatcctcc   300
gtttatttag catcaatgct tgctgccaga ttttccgtgg tcacagtttt acctagaatt   360
aaaacaatgt tagaagacct ggttgattca tacggtatgc aaaaacgtgt agtaaacatc   420
cgtacgacac caatgggcgt attagatttt gagagagatc cagaagcggg aattgaaatg   480
ttaaggcagg aagggaaaag agcggtagag aagataatg cagaagctat tttacttgga   540
tgtgctggta tggcagaatt tgcggatagc cttgaaaaag aattaggagt tcccgttatc   600
gatggagttg tagcgggtgt gaaattcgcc gaagcaattg ttgatctagg aagaaaaaca   660
agtaaactaa aaacttataa atatccagag aaaaaagaat atgttggggc attggagaac   720
tttggcctga atcaaacaac tacaaaataa                                   750
```

<210> SEQ ID NO 3
<211> LENGTH: 40
<212> TYPE: PRT
<213> ORGANISM: Bacillus sp.

<400> SEQUENCE: 3

```
Met Lys Ile Lys Val Ile Asn Pro Asn Thr Thr Leu Ala Met Thr Lys
1                5                  10                  15

Gly Ile Glu His Ala Ala Lys Ser Ala Ala Arg Ser Asp Thr Gln Ile
                20                  25                  30

Val Ala Val Ser Pro Lys Met Gly
                35                  40
```

<210> SEQ ID NO 4
<211> LENGTH: 17
<212> TYPE: DNA
<213> ORGANISM: Artificial Sequence
<220> FEATURE:
<223> OTHER INFORMATION: primer-1
<220> FEATURE:
<221> NAME/KEY: misc_feature
<222> LOCATION: (6)..(6)
<223> OTHER INFORMATION: n represents a,t,g or c.
<220> FEATURE:
<221> NAME/KEY: misc_feature
<222> LOCATION: (12)..(12)
<223> OTHER INFORMATION: n represents a,t,g or c.

<400> SEQUENCE: 4

```
atgacnaarg gnathga                                                  17
```

```
<210> SEQ ID NO 5
<211> LENGTH: 17
<212> TYPE: DNA
<213> ORGANISM: Artificial Sequence
<220> FEATURE:
<223> OTHER INFORMATION: primer-2
<220> FEATURE:
<221> NAME/KEY: misc_feature
<222> LOCATION: (3)..(3)
<223> OTHER INFORMATION: n represents a,t,g or c.
<220> FEATURE:
<221> NAME/KEY: misc_feature
<222> LOCATION: (12)..(12)
<223> OTHER INFORMATION: n represents a,t,g or c.

<400> SEQUENCE: 5
acnccrtcda tnacrgg                                                  17

<210> SEQ ID NO 6
<211> LENGTH: 17
<212> TYPE: DNA
<213> ORGANISM: Artificial Sequence
<220> FEATURE:
<223> OTHER INFORMATION: primer-3

<400> SEQUENCE: 6
taggattcaa ttgaagc                                                  17

<210> SEQ ID NO 7
<211> LENGTH: 17
<212> TYPE: DNA
<213> ORGANISM: Artificial Sequence
<220> FEATURE:
<223> OTHER INFORMATION: primer-4

<400> SEQUENCE: 7
ttgattcata cggtatg                                                  17

<210> SEQ ID NO 8
<211> LENGTH: 30
<212> TYPE: DNA
<213> ORGANISM: Artificial Sequence
<220> FEATURE:
<223> OTHER INFORMATION: primer-5

<400> SEQUENCE: 8
actacacata tgacaattgt tgacccttgg                                    30

<210> SEQ ID NO 9
<211> LENGTH: 30
<212> TYPE: DNA
<213> ORGANISM: Artificial Sequence
<220> FEATURE:
<223> OTHER INFORMATION: primer-6

<400> SEQUENCE: 9
gctaatgaat tcactagtaa gtgaaattcg                                    30

<210> SEQ ID NO 10
<211> LENGTH: 1024
<212> TYPE: DNA
<213> ORGANISM: Bacillus sp.

<400> SEQUENCE: 10
actacacata tgacaattgt tgacccttgg aaaaaacaat caaactaaaa acttataaat   60
cacctgaaaa gaaagaatat agcgggaaat taagaaattt gggtccgtgg aaaaagctat  120
```

```
aaaataaatt cactaaattc taggaggaaa atggttatga aaattaaagt tatcaacccg    180
aatacaactt tggcaatgac aaagggaatt gaacatgctg ctaagtcagc tgcaagatct    240
gatactcaaa ttgttgcagt gagtcctaaa atgggtccgg cttcaattga atcctactat    300
gatgaatatt taagtattcc aggagtaatt gaggaaatta aaaagggaga agaagaagga    360
gtagatgcat ttgttatagc atgctgggga gaccctggat tacatgctgc gagagaagta    420
acagataaac cagttgtagg cattgcgaaa tcctccgttt atttagcatc aatgcttgct    480
gccagatttt ccgtggtcac agttttacct agaattaaaa caatgttaga agacctggtt    540
gattcatacg gtatgcaaaa acgtgtagta aacatccgta cgacaccaat gggcgtatta    600
gattttgaga gagatccaga agcgggaatt gaaatgttaa ggcaggaagg gaaaagagcg    660
gtagaggaag ataatgcaga agctatttta cttggatgtg ctggtatggc agaatttgcg    720
gatagccttg aaaaagaatt aggagttccc gttatcgatg gagttgtagc gggtgtgaaa    780
ttcgccgaag caattgttga tctaggaaag aaaacaagta aactaaaaac ttataaatat    840
ccagagaaaa aagaatatgt tggggcattg gagaactttg gcctgaatca aacaactaca    900
aaataaaaaa ttaattggtt ttggcacaaa aattaaagag ttttcacgct tgttaaatga    960
tagatagttt atatcaattt tatttaattt tgggcgaatt tcacttacta gtgaattcat   1020
tagc                                                                 1024

<210> SEQ ID NO 11
<211> LENGTH: 28
<212> TYPE: DNA
<213> ORGANISM: Artificial Sequence
<220> FEATURE:
<223> OTHER INFORMATION: primer-7

<400> SEQUENCE: 11
ttcatcgcat atgaaaatta aagttatc                                         28

<210> SEQ ID NO 12
<211> LENGTH: 30
<212> TYPE: DNA
<213> ORGANISM: Artificial Sequence
<220> FEATURE:
<223> OTHER INFORMATION: primer-8

<400> SEQUENCE: 12
aagtcagaat tcttattttg tagttgtttg                                       30
```

5-SUBSTITUTED HYDANTOIN RACEMASE, DNA ENCODING THE SAME, RECOMBINANT DNA, TRANSFORMED CELL, AND PROCESS FOR PRODUCTION OF OPTICALLY ACTIVE N-CARBAMYLAMINO ACID OR OPTICALLY ACTIVE AMINO ACID

CROSS-REFERENCES TO RELATED APPLICATIONS

This is a National Stage of International Application No. PCT/JP2006/301253, filed Jan. 26, 2006, the contents of which are incorporated herein by reference. The present application hereby claims priority on Japanese patent application number 2005-022802 filed Jan. 31, 2005, the entire contents of which, including the description, claims, drawings, and abstract, are hereby incorporated by reference.

TECHNICAL FIELD

The present invention relates to a polypeptide having novel hydantoin racemase activity originating in microorganisms, DNA encoding the polypeptide, microorganisms or transformants capable of producing hydantoin racemase, and a process for producing hydantoin racemase using same. The invention also relates to a process for efficiently producing optically active N-carbamylamino acid or optically active amino acid using hydantoin racemase.

BACKGROUND ART

Hydantoin racemase is an enzyme that acts upon optically active 5-substituted hydantoin compounds, or more specifically D- or L-5-substituted hydantoin compounds to catalyze the racemization reaction of these compounds. The enzyme can therefore be used for the production of optically active N-carbamylamino acid or optically active amino acid, which is important as a source material of pharmaceuticals, chemical produces, and food additives, using a 5-substituted hydantoin compound as a starting material.

As shown in Formula (I), in order to produce optically active N-carbamylamino acid from a 5-substituted hydantoin compound, hydantoin racemase is used with hydantoinase having stereoselectivity. In order to produce optically active amino acid from a 5-substituted hydantoin compound, hydantoin racemase is used with hydantoinase having stereoselectivity, as well as N-carbamylamino acid amidohydrolase having or not having stereoselectivity.

The enzyme reactions by hydantoinase and N-carbamylamino acid amidohydrolase may be separately performed in two steps, or alternatively the two enzymes may be mixed together to perform the two reactions in one step.

The decarbamylation reaction following the hydantoinase reaction may alternatively be performed using a decarbamylation method employing conventionally well-known chemical reactions, other than the foregoing method using enzyme.

In the method of reaction using hydantoinase and N-carbamylamino acid amidohydrolase, performing the racemization of the starting 5-substituted hydantoin compound concurrently with the hydantoinase reaction using hydantoin racemase enables the 5-substituted hydantoin compound to be quantitatively converted into optically active N-carbamylamino acid or optically active amino acid, with the result that yield is increased.

Meanwhile, there have been known 5-substituted hydantoin compounds that undergo chemical racemization in the foregoing reaction system. However, they are only limited kinds of such compounds. Further, in many of such 5-substituted hydantoin compounds, the chemical racemization proceeds either slowly or does not proceed at all in practice. As such, a high yield cannot be expected when hydantoin racemase is not used. It is therefore very meaningful to use hydantoin racemase in the present reaction system. Accordingly, a search is underway for hydantoin racemase in order to facilitate racemization of optically active 5-substituted hydantoin compounds, which can be racemized only slowly.

As examples of microorganisms that can produce hydantoin racemase, the microorganisms of the following Genus are known: *Arthrobacter*; (Patent Publication 1, Non-Patent Publication 1); *Pseudomonas* (Patent Publication 2, Non-Patent Publication 2); *Agrobacterium* (Non-Patent Publication 3, Non-Patent Publication 4, Patent Publication 3);

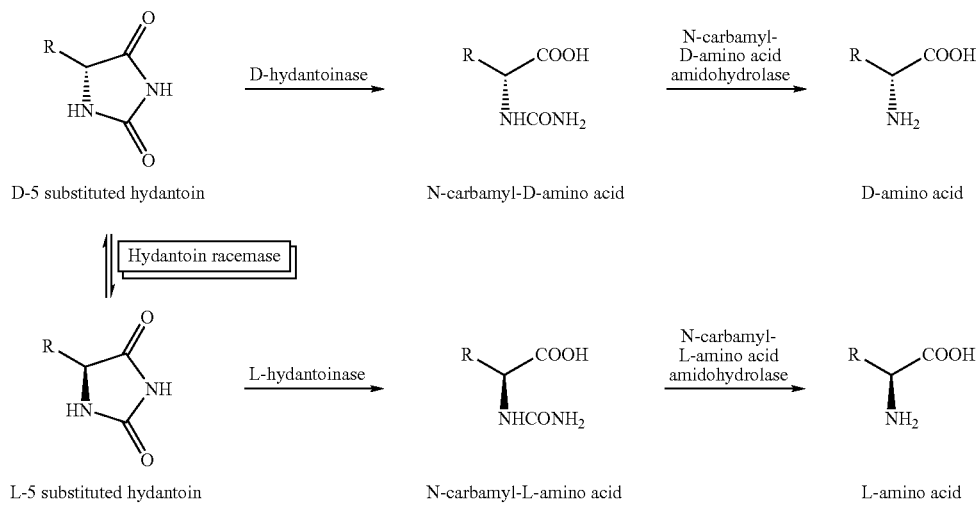

*Sinorhizobium* (Non-Patent Publication 5); *Microbacterium* (Patent Publication 4); *Flavobacterium* (Patent Publication 5); *Pasteurella* (Patent Publication 6); *Candida* (Patent Publication 7).

[Patent Publication 1]
Japanese Laid-Open Patent Publication No. 122591/1987 (Tokukaisho 62-122591)
[Patent Publication 2]
Japanese Laid-Open Patent Publication No. 271784/1992 (Tokukaihei 4-271784)
[Patent Publication 3]
PCT International Publication No. WO03/100050
[Patent Publication 4]
Japanese Laid-Open Patent Publication No. 330784/2002 (Tokukai 2002-330784)
[Patent Publication 5]
Japanese Laid-Open Patent Publication No. 210176/2003 (Tokukai 2003-210176)
[Patent Publication 6]
Japanese Laid-Open Patent Publication No. 210177/2003 (Tokukai 2003-210177)
[Patent Publication 7]
Japanese Laid-Open Patent Publication No. 47194/1986 (Tokukaisho 61-47194)
[Non-Patent Publication 1]
J. Biotechnol., vol. 80, 217 (2000)
[Non-Patent Publication 2]
J. Bacteriol., vol. 174, 7989 (1992)
[Non-Patent Publication 3]
Appl. Microbiol. Biotechnol., 57, 680 (2001)
[Non-Patent Publication 4]
Biotechnol. Prog., 18, 1201 (2002), Biochem. Biophys. Res. Commun. 303, 541 (2003)
[Non-Patent Publication 5]
Appl. Microbiol., 70, 625 (2004)

DISCLOSURE OF INVENTION

Problems to be Solved by the Invention

However, none of the foregoing publications reports enzymes having racemization activity for 5-substituted hydantoins in the production of corresponding unnatural amino acids, for example, such as D-norvaline, D-norleucine, D-penicillamine, D-O-methylserine, and D-homoserine.

It is completely unknown whether bacteria of Genus *Bacillus* have hydantoin racemase activity. Further, there has been no report of purifying and isolating hydantoin racemase to examine its properties. Further, no report has been made for isolation of hydantoin racemase gene.

It is an object of the present invention to provide a novel hydantoin racemase. It is another object of the present invention to identify an amino acid sequence of the hydantoin racemase and a DNA sequence of a gene encoding it, so as to provide microorganisms or transformants capable of producing the enzyme, and a producing process of hydantoin racemase using such microorganisms or transformants.

It is yet another object of the present invention to provide a process for efficiently producing optically active N-carbamylamino acid or optically active amino acid using the hydantoin racemase.

Means for Solving the Problems

In view of the foreign objects, the inventors of the present invention looked into a wide range of soils to search for microorganisms having hydantoin racemase activity, and as a result separated a novel bacterium of Genus *Bacillus* capable of producing a large amount of hydantoin racemase with desirable properties. Hydantoin racemase was isolated and purified from the microorganism, and a hydantoin racemase gene was successfully isolated and expressed in host microorganisms. A hydantoin racemase obtained by the present invention was found to also act upon 5-substituted hydantoin compounds corresponding to the foregoing unnatural amino acids.

The hydantoin racemase so obtained was caused to act upon 5-substituted hydantoin compounds together with hydantoinase or N-carbamylamino acid amidohydrolase. This improved the yield of reactions producing optically active N-carbamylamino acid and optically active amino acid, thereby accomplishing the present invention.

According to one aspect, the present invention provides a polypeptide having hydantoin racemase activity and properties including:

(1) a molecular weight of about 139,000;
(2) a Km value of about 0.304 mM for L-5-(2-methylthioethyl)hydantoin;
(3) an effective temperature range of 25° C. to 65° C. and an optimum temperature of 40° C.;
(4) an effective pH range of 6 to 10 and an optimum pH of 8 to 9;
(5) temperature stability at or below 30° C.; and
(6) pH stability between 4.5 to 8.0.

In another aspect, the present invention provides a polypeptide consisting of an amino acid sequence represented by SEQ ID NO: 1 of the Sequence Listing.

In another aspect, the present invention provides a DNA that encodes the polypeptide.

In another aspect, the present invention provides a recombinant plasmid including the DNA.

In another aspect, the present invention provides a transformant obtained by transforming a host microorganism with the recombinant plasmid.

In another aspect, the present invention provides a microorganism capable of producing the polypeptide and belonging to Genus *Bacillus*.

In another aspect, the present invention provides a process for producing hydantoin racemase, including: culturing a microorganism capable of producing the polypeptide; accumulating the polypeptide in a culture of the microorganism; and collecting the polypeptide.

In another aspect, the present invention provides a process for racemizing optically active 5-substituted hydantoin, including causing an optically active 5-substituted hydantoin compound to be acted upon by the polypeptide having hydantoin racemase activity, the transformant, or the microorganism.

In another aspect, the present invention provides a process for racemizing optically active 5-substituted hydantoin, including causing an optically active 5-substituted hydantoin compound to be acted upon by the polypeptide having hydantoin racemase activity, the transformant, or the microorganism, the optically active 5-substituted hydantoin compound being represented by General Formula (1)

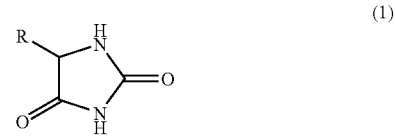

where R represents an alkyl group having 1 to 20 carbon atoms with or without a substituent, an aralkyl group having 7 to 20 carbon atoms with or without a substituent, or an aryl group having 6 to 20 carbon atoms with or without a substituent.

In another aspect, the present invention provides a process for producing optically active N-carbamylamino acid, including causing a 5-substituted hydantoin compound to be acted upon by hydantoinase, together with the polypeptide, the transformant, or the microorganism.

In another aspect, the present invention provides a process for producing optically active N-carbamylamino acid represented by General Formula (2) below,

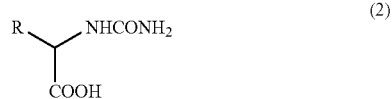

(2)

where R represents an alkyl group having 1 to 20 carbon atoms with or without a substituent, an aralkyl group having 7 to 20 carbon atoms with or without a substituent, or an aryl group having 6 to 20 carbon atoms with or without a substituent, the process including causing a 5-substituted hydantoin compound of General Formula (1) to be acted upon by hydantoinase, together with the polypeptide, the transformant, or the microorganism, In another aspect, the present invention provides a process for producing an optically active amino acid, including causing a 5-substituted hydantoin compound to be acted upon by hydantoinase and N-carbamylamino acid amidohydrolase, together with the polypeptide, the transformant, or the microorganism.

In another aspect, the present invention provides a process for producing an optically active amino acid represented by General Formula (3) below

(3)

where R represents an alkyl group having 1 to 20 carbon atoms with or without a substituent, an aralkyl group having 7 to 20 carbon atoms with or without a substituent, or an aryl group having 6 to 20 carbon atoms with or without a substituent, the process including causing a 5-substituted hydantoin compound of General Formula (1) to be acted upon by hydantoinase and N-carbamylamino acid amidohydrolase, together with the polypeptide, the transformant, or the microorganism.

EFFECTS OF THE INVENTION

A hydantoin racemase of the present invention is an enzyme that can also effectively act upon 5-substituted hydantoin compounds corresponding to unnatural amino acids.

In producing optically active N-carbamylamino acid or optically active amino acid using hydantoinase or N-carbamylamino acid amidohydrolase acting upon 5-substituted hydantoin compounds and in particular 5-substituted hydantoin compounds corresponding to unnatural amino acids, the yield of reaction can be improved by using a hydantoin racemase of the present invention together. With microorganisms and transformants of the present invention, the novel hydantoin racemase can be efficiently produced. With a hydantoin racemase of the present invention or microorganisms producing the hydantoin racemase, optically active N-carbamylamino acid or optically active amino acid can be efficiently produced.

BEST MODE FOR CARRYING OUT THE INVENTION

Figure 1:
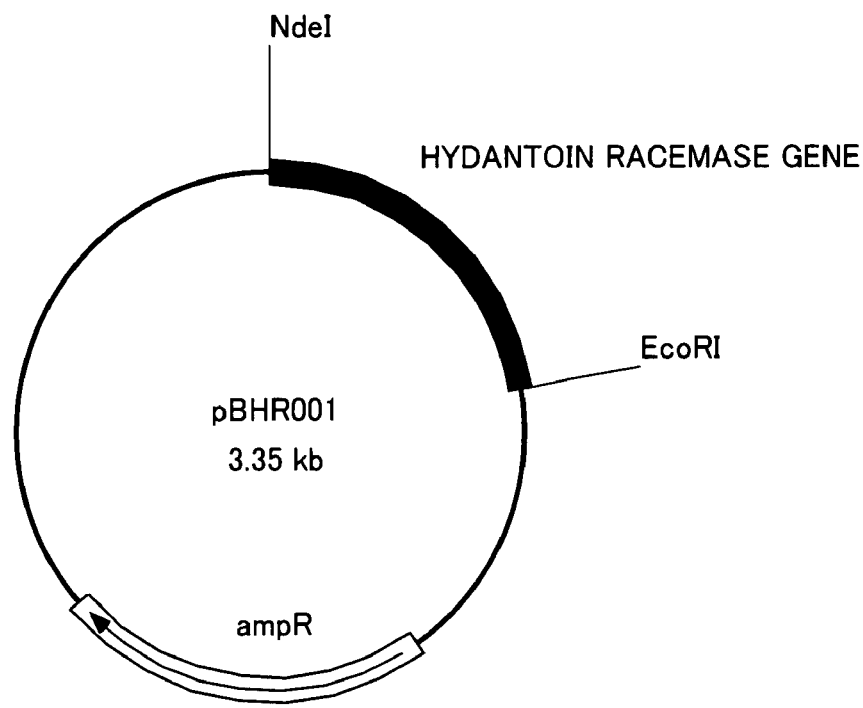
FIG. 1 is a diagram showing a restriction enzyme map of recombinant plasmid pBHR001 including a hydantoin racemase gene according to an embodiment of the present invention.

The following will describe the present invention in detail based on an embodiment.

1. Polypeptide

First, description is made as to a polypeptide according to an embodiment of the present invention. A polypeptide of the present invention has hydantoin racemase activity and the following physical and chemical properties.

1) Action

The polypeptide catalyzes the racemization reaction of optically active 5-substituted hydantoin compounds.

2) Molecular Weight

About 139,000

3) Km Value for L-5-(2-methylthioethyl)hydantoin

About 0.304 mM

4) Effective Temperature Range

Temperature range: 25° C. to 65° C.; optimum temperature: 40° C.

5) Effective pH Range pH range: 6 to 10; optimum pH range 8 to 9

6) Temperature Stability

30° C. or below 7) pH Stability pH 4.5 to 8.0

The polypeptide also has the following physical and chemical properties.

8) Relative Activity 24.2 units per 1 mg of pure enzyme (1 unit is defined as the amount of enzyme that generates 1 μmol D-5-(2-methylthioethyl)hydantoin per minute, as will be described later in connection with the measurement method)

9) Substrate Inhibition

The polypeptide is subject to substrate inhibition when 50 to 80 mM L-5-(2-methylthioethyl)hydantoin is used as a substrate In an embodiment of the present invention, the hydantoin racemase activity of the polypeptide can be measured by, for example, quantification of D-5-(2-methylthioethyl)hydantoin generated at 30° C. in 30 minutes in 50 mM Tris (tris (hydroxymethyl)aminomethane)-HCl buffer (pH 7.5) containing 50 mM L-5-(2-methylthioethyl)hydantoin, using high-performance liquid chromatography (HPLC) or the like.

The hydantoin racemase of an embodiment of the present invention (hereinafter referred to as "present enzyme" or "present hydantoin racemase") is a novel hydantoin racemase which, in terms of origin, property, and other criteria, clearly distinguishes over the known hydantoin racemases described in conjunction with the BACKGROUND ART section.

(i) The present enzyme has the amino acid sequence sharing 50% homology with the amino acid sequence of the hydantoin racemase originating in *Agrobacterium radiobacter* (International Publication WO03/100050). Therefore, the two amino acid sequences do not match completely. The present enzyme also differs from the hydantoin racemase originating in *Agrobacterium radiobacter* in terms of substrate inhibition, which is effected on the former but not on the latter.

(ii) The present enzyme has the amino acid sequence sharing 48% homology with the amino acid sequence of the hydantoin racemase of *Microbacterium liquefaciens* (Tokukai 2002-330784). Therefore, the two amino acid sequences do not match completely. The present enzyme also differs from the hydantoin racemase of *Microbacterium liquefaciens* in terms of optimum temperature, which is about 40° C. in the former and 50° C. to 60° C. in the latter.

(iii) The present enzyme differs from the hydantoin racemase of *Pseudomonas* sp. (Tokukaihei 4-271784, J. Bacteriol., vol. 174, 7989 (1992)) in three amino acid residues. The present enzyme also differs from the hydantoin racemase of *Pseudomonas* sp. in terms of optimum temperature and optimum pH, which are 40° C. and 8 to 9 in the former and 45° C. and 9.5 in the latter. The hydantoin racemase of *Pseudomonas* sp. exhibits strong racemization activity for L-5-(1-methylpropyl)hydantoin as it does for L-5-(2-methylthioethyl)hydantoin. Specifically, the relative activity for the substrate L-5-(1-methylpropyl)hydantoin is 132 with respect to the relative activity of 100 for the substrate L-5-(2-methylthioethyl)hydantoin (see the proportion of D-form at the reaction time of 10 minutes in Table 1 of Tokukaihei 4-271784).

On the other hand, the present enzyme has the relative activity of 2 for the substrate L-5-(1-methylpropyl)hydantoin with respect to the relative activity of 100 for L-5-(2-methylthioethyl)hydantoin to which the present enzyme shows strong racemization activity (see Table 2 of Example 2). The present enzyme therefore greatly differs from the hydantoin racemase of *Pseudomonas* sp. also in terms of substrate specificity, in addition to optimum temperature and pH. The properties of the two enzymes are clearly different.

Conventionally, it had not been known whether microorganisms belonging to Genus *Bacillus* had hydantoin racemase activity. The hydantoin racemase of an embodiment, obtained by the inventors of the present invention is a novel enzyme originating in microorganisms belonging to Genus *Bacillus*, in which the presence or absence of hydantoin racemase activity had not been known. The inventors of the present invention has revealed for the first time that the present hydantoin racemase was an enzyme with the properties different from those found in known hydantoin racemases, and that the present hydantoin racemase also acted on 5-substituted hydantoin compounds corresponding to unnatural amino acids (see Table 2 of Example 2).

2. Microorganisms

A polypeptide according to an embodiment of the present invention can be obtained preferably from microorganisms belonging to Genus *Bacillus*, and more preferably from *Bacillus* sp. KNK519HR.

*Bacillus* sp. KNK519HR is a bacterial strain isolated and obtained by the inventors according to the present invention. *Bacillus* sp. KNK519HR was deposited on Dec. 12, 2005 at the International Patent Organism Depository (IPOD), the National Institute of Advanced Industrial Science and Technology, whose address is Tsukuba Central 6, 1-1-1 Higashi, Tsukuba, Ibaraki, Japan, 305-8566, and has been assigned depository accession number FERM BP-10477 (domestically deposited strain originally deposited on Dec. 15, 2004 was transferred to the International Depository Authority under Budapest Treaty). The following lists microbiological properties of *Bacillus* sp. KNK519HR.

1. Morphology

1) A *bacillus* of the size of about 1.0 to 1.1 μm (diameter)× 2.0 to 4.0 μm

2) Gram staining: Positive

3) Mortility: Yes

4) Spores: present

5) Colony morphology on agar plate culture: circular, undulate, convex, glossy, yellow 2. Culture Properties 1) Growth temperature test: 37° C.(+), 45° C.(−)

3. Physiological Properties

1) Catalase: +

2) Oxydase: −

3) Acid/gas production (acid production/gas production) from glucose: −/−

4) O/F test (oxidization/fermentation): −/−

5) Fermentation test

Glycerol: +
Erythritol: −
D-Arabinose: −
L-Arabinose: −
Ribose: +
D-Xylose: +
L-Xylose: −
Adonitol: −
β-Methyl-D-xylose: −
Galactose: +
Glucose: +
Fructose: +
Mannose: −
Sorbose: −
Rhamnose: −
Dulcitol: −
Inositol: −
Mannitol: +

Sorbitol: −
α-Methyl-D-mannose: −
α-Methyl-D-glucose: −
N-Acetylglucosamine: +
Amygdalin: −
Arbutin: +
Esculin: +
Salicin: +
Cellobiose: +
Maltose: +
Lactose: −
Melibiose: −
Saccharose: +
Trehalose: +
Inulin: −
Melezitose: −
Raffinose: +
Starch: +
Glycogen: +
Xylitol: −
Gentiobiose: −
D-Turanose: −
D-Lyxose: −
D-Tagatose: −
D-Fucose: −
L-Fucose: −
D-Arabitol: −
L-Arabitol: −
Gluconate: −
2-Ketogluconic acid: −
5-Ketogluconic acid: −

6) Biochemical Test
β-Galactosidase: −
Arginine dihydrolase: −
Lycine decarboxylase: −
Ornithine decarboxylase: −
Use of citric acid: −
$H_2S$ production: −
Urease: −
Tryptophan deaminase: −
Indole production: −
Acetoin production (VP): −
Gelatinase: +
Reduction of nitrate: −

7) Growth Under Anaerobic Conditions: −

8) Growth Under 10% NaCl: +

9) Hippurate Hydrolysis: −

10) Casein Hydrolysis: +

From these microbiological properties and analysis of 16SrDNA sequence, Strain KNK519HR was identified as *Bacillus* sp.

The microorganism producing a polypeptide of the present invention may be a wildtype strain or a mutant strain. The mutant strain can be obtained by methods known to a person ordinary skill in the art, by treating Strain KNK519HR with UV irradiation, or chemicals such as N-methyl-N'-nitro-N-nitrosoguanidine (NTG) or ethylmethane sulfonate (EMS), for example.

The medium for culturing the microorganism producing a polypeptide of the present invention is not particularly limited as long as the microorganism can grow therein. For example, common liquid media may be used that contain, as a carbon source, sugars such as glucose and sucrose; alcohols such as ethanol and glycerol; fatty acids such as oleic acid and stearic acid, and esters thereof; and oils such as rapeseed oil and soybean oil, and, as a nitrogen source, ammonium sulfate, sodium nitrate, peptone, casamino acid, corn steep liquor, bran, or yeast extract, and, as an inorganic salt, magnesium sulfate, sodium chloride, calcium carbonate, dipotassium hydrogen phosphate, or potassium dihydrogen phosphate, and, as other nutrients, malt extract or meat extract. To enhance hydantoin racemase production, the medium may be supplemented with a small amount of 5-substituted hydantoin compound. The supplement is added to the medium in a concentration range selected from the group consisting of no less than 0.001 weight % and no greater than 10 weight %, and preferably no less than 0.01 weight % and no greater than 1 weight %.

Culturing can be performed aerobically in a temperature range of generally no less than 20° C. and no greater than 40° C., and preferably no less than 25° C. and no greater than 35° C., and a pH range of generally no less than 6 and no greater than 8, and preferably no less than 6.5 and no greater than 7.5. Culture time is generally about 1 day to 5 days. The culture method may be batch-wise or continuous.

3. Enzyme Purification

Separation and purification of the hydantoin racemase may be performed as follows. First, after culturing, the cells are collected from the culture by a method such as centrifugation. The cells are then disrupted with a sonicator or other means to obtain a crude enzyme solution. The crude enzyme solution is purified by a method such as salting-out or column chromatography to obtain a purified hydantoin racemase.

A polypeptide of the present invention is obtained in the manner described above, by culturing microorganisms capable of producing hydantoin racemase and collecting the hydantoin racemase accumulated in the microorganisms. A polypeptide of the present invention may be an enzyme obtained from microorganisms as described above, or an enzyme produced by transformants obtained by gene recombination techniques, as will be described later. An enzyme according to an embodiment of the present invention is a polypeptide with the amino acid sequence of SEQ ID NO: 1 of the Sequence Listing.

4. DNA

The following will describe DNA of the present invention. A DNA of the present invention is a DNA encoding a polypeptide having the hydantoin racemase activity as described above. Preferably, a DNA of the present invention is a DNA encoding the amino acid sequence of SEQ ID NO: 1 of the Sequence Listing. For example, a DNA of the present invention is a DNA with the base sequence of SEQ ID NO: 2 of the Sequence Listing. As a rule, a single amino acid corresponds to different codons. As such, base sequences encoding the amino acid sequence of SEQ ID NO: 1 are equivalent to the base sequence of SEQ ID NO: 2, and DNA with such base sequences are also defined as a DNA of the present invention.

As used herein, "base sequences equivalent to a specific base sequence" refers to, for example, base sequences that encode the amino acid sequence corresponding to the specific base sequence, but that are different from the specific base sequence. Further, the "equivalent base sequence" refers to the base sequence with a substitution, insertion, deletion, and/or addition of one or several bases in the specific base sequence, and with the peptide activity (for example, hydantoin racemase activity) of the peptide encoded by the specific base sequence. Further, "several bases" refers to preferably no greater than 10 bases, and more preferably no greater than 9, 8, 7, 6, 5, 4, 3, or 2 bases.

The DNA including a hydantoin racemase gene according to an embodiment of the present invention may be obtained from, for example, *Bacillus* sp. KNK519HR, or may be chemically synthesized. The following describes an example of obtaining target DNA.

First, the N-terminus amino acid sequence of hydantoin racemase purified from a microorganism having hydantoin racemase activity is determined using a vapor-phase protein sequencer or the like. Then, DNA primers are synthesized that are designed based on the N-terminus amino acid sequence and the homologous sequence of known hydantoin racemase.

Next, chromosomal DNA is isolated from the source microorganism of hydantoin racemase. Chromosomal DNA is obtained from cultured cells by using a UltraClean Microbial DNA Isolation Kit (MO BIO Laboratories, Inc.)

Using the chromosomal DNA as a template, PCR is run with the DNA primers prepared as above. This produces part of the target gene.

Next, DNA fragments encoding portions facing toward the N- and C-termini from the partial gene are obtained by an inverse PCR method (see Nucleic Acids Res. 16, 8186 (1988), for example). After determining base sequences of the DNA fragments, DNA primers are prepared based on the base sequence of the portion that presumably lies upstream of the enzyme N-terminus, and the base sequence of the portion that presumably lies downstream of the enzyme C-terminus. Using the DNA primers, PCR is run with the chromosomal DNA as a template. As a result, DNA fragments including a full-length target hydantoin racemase gene are obtained.

Next, the DNA fragments including the hydantoin racemase gene are ligated to a vector DNA using T4 DNA ligase or the like and a recombinant plasmid was obtained. The plasmid is then used to analyze base sequences of the DNA fragment portions including the hydantoin racemase gene introduced in the vector, and the presence of a coding base sequence of the N-terminus amino acid sequence of the hydantoin racemase is confirmed. From this, a translation start site and a stop codon are confirmed to determine an open reading frame.

The DNA so obtained or a recombinant plasmid prepared by introducing the DNA into the vector is used to transform host microorganisms and obtain transformants.

5. Host and Vector

As the host and vector, the host-vector system described in *Recombinant DNA Experiment Guidelines* (*Kumikae DNA Jikken Shishin*) (*Kagaku Gijyutsu Cho, Kenkyu Kaihatsushitsu, Life Science*, revised on Mar. 22, 1996) may be used. For example, the host may be a microorganism of Genus *Escherichia, Pseudomonas, Flavobacterium, Bacillus, Serratia, Corynebacterium, Brevibacterium, Agrobacterium, Acetobacter, Gluconobacter, Lactobacillus, Streptococcus*, or *Streptomyces*.

The vector may be a plasmid, a phage, or a derivative thereof originating in microorganisms, capable of self-replication in the host. It is preferable that *Escherichia coli* be used as the host microorganism, and that the vector be capable of self-replication in *Escherichia coli*. As such vectors, those readily available to a person ordinary skill in the art or those commercially available may be used, including, for example, pUC18 (Takara Bio Inc.), pUC19 (Takara Bio Inc.), pBR322 (Takara Bio Inc.), pACYC184 (Nippon Gene Co., Ltd.), pSC101 (Funakoshi Corporation), pT7Blue (Takara Bio Inc.), and pUCNT which can be produced by a person ordinary skill in the art according to the teaching of International Publication WO94/03613, or derivatives of these vectors.

Further, a vector may be used that has been modified to have a strong constitutive promoter for enhancing enzyme production.

6. Transformant

As an example of a transformant, transformed *Escherichia coli* HB101 (pBHR001) is obtained by transforming *Escherichia coli* HB101 with the recombinant plasmid pBHR001 (FIG. 1) that has been prepared by inserting the target DNA into pUCNT. Plasmid pBHR001 is specified by the restriction map shown in FIG. 1.

The transformed *Escherichia coli* HB101 (pBHR001) obtained according to this method was deposited on Dec. 12, 2005 at the International Patent Organism Depositary (IPOD), the National Institute of Advanced Industrial Science and Technology, whose address is Tsukuba Central 6, 1-1-1 Higashi, Tsukuba, Ibaraki, Japan, 305-8566, and has been assigned depository accession number FERM BP-10476 (domestically deposited strain originally deposited on Dec. 15, 2004 was transferred to the International Depository Authority under Budapest Treaty).

Note that, the recombinant DNA technique used in the present invention is known in the art, and described, for example, in Molecular Cloning 2nd Edition (Cold Spring Harbor Laboratory Press, 1989), Current Protocols in Molecular Biology (Greene Publishing Associates and Wiley-Interscience).

The transformant is cultured using common culture medium. Common culture medium should contain nutrients such as a carbon source, a nitrogen source, and an inorganic salt. Desirable results are often obtained by supplementing the culture medium with a trace amount of organic nutrients such as vitamins and amino acids. Suitable examples of a carbon source are carbohydrates such as glucose or sucrose; organic acids such as acetic acid; and alcohols. Examples of a nitrogen source include: ammonium salt, aqueous ammonia, ammonia gas, urea, yeast extract, peptone, and corn steep liquor. Examples of an inorganic salt include: phosphate, magnesium salt, potassium salt, sodium salt, calcium salt, iron salt, sulfate salt, and chlorine.

Culturing is performed in a temperature range of generally 25° C. to 40° C., and more preferably 25° C. to 37° C. A pH range of culturing is generally 4 to 8, and preferably 5 to 7.5. The culture method may be batch-wise or continuous. As required, an enzyme inducing process may be performed, for example, by adding isopropyl-1-thio-$\beta$-D-galactoside (IPTG) or lactose.

7. Method of Producing Optically Active N-carbamylamino Acid or Optically Active Amino Acid The following will describe a method for efficiently producing optically active N-carbamylamino acid or optically active amino acid, using hydantoin racemase of the present invention. An optically active N-carbamylamino acid according to an embodiment of the present invention can be produced by conversion from a 5-substituted hydantoin compound in the reaction catalyzed by hydantoinase, according to the method represented by Reaction Formula (I). The N-carbamylamino acid so produced can be converted into the amino acid by hydrolysis under the action of carbamylamino acid amidohydrolase, according to the method represented by Reaction Formula (I). Here, by using hydantoin racemase together, the optically active N-carbamylamino acid or optically active amino acid can be produced both efficiently and quantitatively from the 5-substituted hydantoin compound, which has a slow chemical racemization rate.

In order to produce the optically active N-carbamylamino acid, it is important in the present invention that the hydantoin racemase of the present invention be used together with hydantoinase having stereoselectivity. In producing the optically active amino acid, the hydantoin racemase of the present invention and the hydantoinase having stereoselectivity may be used together to first produce optically active N-carbamylamino acid, which is then converted into the amino acid by using N-carbamylamino acid amidohydrolase or by chemical decarbamylation. Alternatively, the amino acid may be produced by using the hydantoin racemase of the present invention together with hydantoinase and N-carbamylamino acid amidohydrolase. When using hydantoinase and N-carbamylamino acid amidohydrolase together, the optically active amino acid can be obtained when only one of the enzymes has stereoselectivity.

8. Hydantoinase

The hydantoinase is an enzyme with the activity to hydrolyze a derivative of 5-substituted hydantoin to produce a derivative of N-carbamylamino acid. The hydantoinase used in the present invention may originate in animals, plants, or microorganisms, among which those originating in microorganisms are preferable for industrial use. Any microorganism may be used as long as it is capable of producing the enzyme. The following lists some of the microorganisms that are known to be capable of producing the enzyme.

As the hydantoinase that catalyzes D-form selective hydrolysis, those originating in the following microorganisms may be used. Bacteria of Genus *Acetobacter, Achromobacter, Aerobacter, Agrobacterium, Alcaligenes, Arthrobacter, Bacillus, Brevibacterium, Corynebacterium, Enterobacter, Erwinia, Escherichia, Klebsiella, Microbacterium, Micrococcus, Protaminobacter, Proteus, Pseudomonas, Sartina, Serratia, Xanthomonas, Aeromonas, Flavobacterium, Rhizobium*. Actinomycetes of Genus *Actinomyces, Mycobacterium, Nocardia, Streptomyces, Actinoplanes, Rhodococcus*. Molds of Genus *Aspergillus, Paecilomyces, Penicillium*. Yeasts of Genus *Candida, Phichia, Rhodotorula, Torulopsis*.

Among these examples, hydantoinase originating in *Agrobacterium, Bacillus, Pseudomonas*, and *Rhizobium* is preferable.

More preferable is hydantoinase originating in *Agrobacterium* sp. KNK712 (FERM BP-1900), *Bacillus* sp. KNK245 (FERM BP-4863), *Pseudomonas putida* IFO12996, *Pseudomonas* sp. KNK003A (FERM BP-3181), and *Rhizobium* sp. KNK1415 (FERM BP-4419).

As the hydantoinase that catalyzes L-form selective hydrolysis, those originating in *Bacillus, Flavobacterium, Arthrobacter, Pseudomonas*, and *Nocardia* may be used.

Cells that exhibit strong activity to efficiently produce hydantoinase at high yield can be effectively obtained by producing transformed microorganisms as known in the art. A method of producing such microorganisms is taught in International Publication WO96/20275, for example. As taught in this publication, hydantoinase gene is first cloned from bacterial strains having hydantoinase activity, and the gene is inserted into a vector to produce a recombinant plasmid, which is then used to transform suitable host cells. The recombinant DNA technique is known in the art.

Examples of such transformants that produce D-form selective hydantoinase at high yield include: *Escherichia coli* HB101 pTH104 (FERM BP-4864) containing a hydantoinase gene originating in *Bacillus* sp. KNK245 (FERM BP-4863); *Escherichia coli* HB101 pAH1043 (FERM BP-4865) containing a hydantoinase gene originating in *Agrobacterium* sp. KNK712 (FERM BP-1900); and *Escherichia coli* HB101 pPHD301 (FERM BP-4866) containing a hydantoinase gene originating in *Pseudomonas* sp. KNK003A (FERM BP-3181), as disclosed in International Publication WO96/20275.

The production of hydantoinase by the transformants, or the production of hydantoinase by the bacterial strains having hydantoinase activity may be performed using common nutrient medium as taught in, for example, International Publication WO96/20275. As required, an enzyme inducing process may be performed.

9. N-Carbamylamino Acid Amidohydrolase

N-carbamylamino acid amidohydrolase is an enzyme that exerts its action in the hydrolysis of the N-carbamylamino acid derivative to produce the amino acid derivative. As with hydantoinase, the N-carbamylamino acid amidohydrolase used in the present invention may originate in animals, plants, or microorganisms, among which those originating in microorganisms are preferable for industrial use. Any microorganism may be used as a source of enzyme as long as it is capable of producing the enzyme.

The following lists examples of microorganisms that have been conventionally used as a source of D-form selective N-carbamylamino acid amidohydrolase. *Achromobacter, Aerobacter, Aeromonas, Agrobacterium, Alcaligenes, Arthrobacter, Bacillus, Blastobacter, Bradyrhizobium, Brevibacterium, Comamonas, Flavobacterium, Moraxella, Paracoccus, Pseudomonas, Rhizobium, Serratia,* and *Sporosarcina*, as taught in Japanese Examined Patent Publication (Tokukosho) No. 57-18793, Japanese Examined Patent Publication (Tokukosho) No. 63-20520, Japanese Examined Patent Publication (Tokukohei) No. 1-48758, and Japanese Laid-Open Patent Publication (Tokukaihei) No. 6-233690.

Among these examples, microorganisms of Genus *Agrobacterium, Blastobacter, Comamonas, Pseudomonas*, and *Rhizobium* are preferable as a source of the enzyme.

*Agrobacterium* sp. KNK712 (FERM BP-1900), *Rhizobium* sp. KNK1415 (FERM BP-4419), and *Pseudomonas* sp. KNK003A (FERM BP-3181) are more preferable as a source of N-carbamylamino acid amidohydrolase.

*Arthrobacter, Microbacterium*, and *Pseudomonas* are examples of microorganisms that have been conventionally used as a source of N-carbamylamino acid amidohydrolase that catalyzes the L-form selective hydrolysis.

The microorganisms as exemplified above may be wild-type strains or mutant strains that have been mutated to improve N-carbamylamino acid amidohydrolase activity. Further, the microorganisms may be transformants that have been obtained to produce N-carbamylamino acid amidohydrolase at high yield.

Transformed microorganisms that efficiently produce N-carbamylamino acid amidohydrolase at high yield are obtained by a method taught in International Publication WO92/10579, for example. As taught in this publication, N-carbamylamino acid amidohydrolase gene is first cloned from bacterial strains having N-carbamylamino acid amidohydrolase activity, and the gene is inserted into a vector to produce a recombinant plasmid, which is then used to transform suitable host cells.

Examples of such transformants that produce D-form selective N-carbamylamino acid amidohydrolase at high yield include: *Escherichia coli* JM109 (pAD108) (FERM BP-3184) containing an N-carbamylamino acid amidohydrolase gene originating in *Agrobacterium* sp. KNK712 (FERM BP-1900) described in International Publication WO92/10579, *Escherichia coli* JM109 (pPD304) (FERM BP-3183) containing an N-carbamylamino acid amidohydrolase gene originating in *Pseudomonas* sp. KNK003A (FERM BP-3181), and *Escherichia coli* HB101 (pNT4553) (FERM BP-4368) containing an N-carbamylamino acid amidohydrolase gene originating in *Agrobacterium* sp. KNK712 (FERM BP-1900) that have been genetically modified to improve heat resistance as described in International Publication WO94/03613.

The production of N-carbamylamino acid amidohydrolase may be performed by culturing microorganisms having N-carbamylamino acid amidohydrolase activity, and transformants thereof using common culture methods. Culturing is generally performed using liquid nutrient medium, but solid surface culture may be used as well. Medium is supplemented with a normally utilized carbon source, nitrogen source, and inorganic salt nutrients essential for microbial growth.

It is preferable that accumulation of N-carbamylamino acid amidohydrolase be enhanced by adding a small amount of (i) amino acids such as 4-hydroxyphenylglycine and phenylglycine; (ii) N-carbamyl-α-amino acids such as N-carbamyl-methionine and N-carbamyl-phenylalanine; (iii) 5-substituted hydantoins such as 5-(4-hydroxyphenyl)hydantoin and 5-phenylhydantoin; (iv) pyrimidine metabolites such as uracil, dihydrouracil, and β-ureidopropionic acid; (v) urea; (vi) metal ions such as $Fe^{2+}$, $Fe^{3+}$, $Be^{2+}$, $Co^{2+}$, $Al^{3+}$, $Li^+$, $Mn^{2+}$, $Mg^{2+}$, and $Cs^+$; or (vii) enzyme inducing agents such as isopropyl-1-thio-β-D-galactoside (IPTG) and lactose. The concentration of such substance enhancing production of N-carbamylamino acid amidohydrolase in medium is selected from a range of no less than 0.1 mM and no greater than 10 mM for metal ions, and no less than 0.01 weight % and no greater than 1 weight % for other substances.

Culturing is performed in a temperature range of generally no less than 20° C. and no greater than 85° C., and preferably no less than 25° C. and no greater than 60° C., and a pH range of generally no less than 4 and no greater than 11, and preferably no less than 5 and no greater than 9. Microbial growth may be facilitated by aeration and agitation.

10. Enzyme

In the present invention, the hydantoin racemase, hydantoinase, and N-carbamylamino acid amidohydrolase may be used in the form of microorganisms having the enzyme activity, or processed products of such microorganisms, in addition to be used as enzymes per se. As used herein, the "processed products of microorganisms" means crude extracts, freeze-dried cultured cells, acetone-dried cells, or disrupted cells of these processed products.

Further, the enzymes may be used as fixed enzymes that are prepared by fixing the enzymes either directly or in the form of microorganisms, using known means. Fixation may be performed by methods known in the art, for example, such as a crosslinking method, a covalent bonding method, a physical adsorption method, and entrapment. Suitable examples of a support used to fix the enzymes include: phenol formaldehyde anion exchange resin such as Duolite A-568 or DS-17186 (Rohm and Haas Company: registered trademarks); and various kinds of anion exchange resins with various amines or ammonium salts or diethanol amine functional groups, as represented by polystyrene resins such as Amberlite IRA935, IRA945, IRA901 (Rohm and Haas Company: registered trademarks), Lewatit OC1037 (Bayer: registered trademark), and Diaion EX-05 (Mitsubishi Chemical Corporation: registered trademark). A support made of DEAE-cellulose or the like may be used as well.

11. Enzyme Reaction

In an embodiment of the present invention, the enzyme reaction may be performed as follows. In the present invention, the 5-substituted hydantoin compound used as the substrate of enzyme reaction may be any of a D-form, an L-form, a racemate, and a mixture of D-form and L-form of arbitrary proportions. As the substrate of enzyme reaction, a 5-substituted hydantoin compound may be used, and preferably a 5-substituted hydantoin compound represented by General Formula (1) is used.

Here, R represents an alkyl group having 1 to 20 carbon atoms with or without a substituent, an aralkyl group having 7 to 20 carbon atoms with or without a substituent, or an aryl group having 6 to 20 carbon atoms with or without a substituent. The alkyl group of R having 1 to 20 carbon atoms with or without a substituent may be, but is not particularly limited to, a methyl group, an isopropyl group, an isobutyl group, a 1-methylpropyl group, a carbamoyl methyl group, a 2-carbamoyl ethyl group, a hydroxymethyl group, a 1-hydroxyethyl group, a mercaptomethyl group, a 2-methylthioethyl group, a (1-mercapto-1-methyl)ethyl group, a carboxymethyl group, a 2-carboxyethyl group, a 4-aminobutyl group, a 3-guanidinopropyl group, a 4(5)-imidazole methyl group, an ethyl group, an n-propyl group, an n-butyl group, a methoxymethyl group, a 2-hydroxyethyl group, a 3-aminopropyl group, a 2-cyanoethyl group, 3-cyanopropyl group, 4-(benzoylamino)butyl group, or a 2-methoxycarbonyl ethyl group, for example. The aralkyl group having 7 to 20 carbon atoms with or without a substituent may be, but is not particularly limited to, a benzyl group, an indolylmethyl group, a 4-hydroxybenzyl group, or a 3,4-methylenedioxybenzyl group, for example. The aryl group having 6 to 20 carbon atoms with or without a substituent may be, but is not particularly limited to, a phenyl group or a 4-hydroxyphenyl group, for example.

Using the substrate, the reaction is performed in an aqueous medium in the presence of the hydantoin racemase, together with the stereoselective hydantoinase, or together with hydantoinase and N-carbamylamino acid amidohydrolase. The reaction is performed in a solution or suspension of substrate charged to a concentration of no less than 0.1% (w/v) and no greater than 90% (w/v), and more preferably no less than 1% (w/v) and no greater than 60% (w/v). The solution or suspension is tentatively allowed to stand or stirred at a reaction temperature of no less than 10° C. and no greater than 80° C., and preferably no less than 20° C. and no greater than 60° C., and at a pH of no less than 4 and no greater than 9, and preferably no less than 5 and no greater than 8. The substrate may be added continuously. The reaction may be performed either in batch or continuously. The reaction of the present invention may also be performed using a fixed enzyme and a membrane reactor, etc.

The aqueous medium is suitably selected and may be water or a buffer, or a mixture of water or buffer with a water-soluble solvent such as ethanol. Alternatively, the aqueous medium may be a solvent of bilayer system, including an aqueous solvent and an organic solvent, for example, such as ethyl acetate, butyl acetate, toluene, chloroform, or n-hexane, which does not easily mix with water. As required, the aqueous medium may be supplemented with an antioxidant, a detergent, a coenzyme, or metal, for example.

In sum, in the racemization of 5-substituted hydantoin compound with the hydantoin racemase of the present invention, only one of the optically active forms of the 5-substituted hydantoin compound is hydrolyzed by the stereoselective hydantoinase and converted to optically active N-carbamylamino acid. As required, the optically active N-carbamylamino acid is further converted to an optically active amino acid by using N-carbamylamino acid amidohydrolase. The optically active amino acid may alternatively be obtained by a chemical decarbamylation reaction, without using N-carbamylamino acid amidohydrolase.

The optically active N-carbamylamino acids and optically active amino acids so obtained can be isolated and purified by ordinary separation methods, for example, such as extraction, concentration, crystallization, or column chromatography, or by a combination of these methods.

The optically active N-carbamylamino acid obtained by a producing method according to an embodiment of the present invention is represented by, for example, General Formula (2). Specific examples are N-carbamyl-D-leucine, N-carbamyl-D-isoleucine, N-carbamyl-D-valine, N-carbamyl-D-norleucine, N-carbamyl-D-norvaline, N-carbamyl-D-methionine, N-carbamyl-D-cysteine, N-carbamyl-D-penicillamine, N-carbamyl-D-phenylalanine, N-carbamyl-D-phenylglycine, and N-carbamyl-D-4-hydroxyphenylglycine. The optically active amino acid obtained by a producing method according to an embodiment of the present invention is represented, for example, by General Formula (3). Specific examples include: D-leucine, D-isoleucine, D-valine, D-norleucine, D-norvaline, D-methionine, D-cysteine, D-penicillamine, D-phenylalanine, D-phenylglycine, and D-4-hydroxyphenylglycine.

EXAMPLES

The following describes specific examples of the present invention. The present invention is not limited by the examples below.

Example 1

Purification of Hydantoin Racemase

*Bacillus* sp. KNK519HR (FERM BP-10477) was inoculated in medium (500 ml Sakaguchi flask) with the composition shown in Table 1. The cells were cultured aerobically at 30° C. for 17 hours with shaking.

TABLE 1

| | |
|---|---|
| Glycerin | 1.0% |
| Glucose | 0.5% |
| $KH_2PO_4$ | 0.454% |
| $Na_2HPO_4$ | 0.620% |
| $(NH_4)_2SO_4$ | 0.65% |
| $MgSO_4 \cdot 7H_2O$ | 0.05% |
| $MnCl_2 \cdot 4H_2O$ | 0.002% |
| $FeSO_4 \cdot 7H_2O$ | 0.002% |
| $CaCl_2 \cdot 2H_2O$ | 0.002% |
| Citrate•Na•$2H_2O$ | 0.032% |
| Yeast extract | 0.1% |
| DL-5-(2-Methylthioethyl) hydantoin | 0.05% |
| DL-5-Methyl hydantoin | 0.05% |
| DL-5-Benzyl hydantoin | 0.05% |

The medium was adjusted to pH 7 and sterilized with an autoclave prior to use. The glucose was sterilized separately from the other components and added to the medium after sterilization. The volume of medium in the flask was 300 ml.

After culturing, the cells were collected by centrifugation and suspended in a 50 mM potassium phosphate buffer (pH 7.0) containing 1 mM dithiothreitol (DTT). After sonicating the cells, the cells were centrifuged again and the supernatant was obtained as a crude enzyme solution. Then, ammonium sulfate was added to the crude enzyme solution to 60% to 90% saturation, and the salt-out precipitate was obtained by centrifugation. The precipitate was dissolved in a 50 mM potassium phosphate buffer (pH 7.0) containing 1 mM DTT and dialyzed with the same buffer. This was followed by column chromatography using a TSKgel DEAE Toyopearl 650M (Tosoh Corporation), in which elution was performed with a 50 mM potassium phosphate buffer (pH 7.0) containing 1 mM DTT, under 0 to 0.6 M NaCl gradient. As a result, active fractions were obtained. The fractions were supplemented with ammonium sulfate to 1.5 M, and column chromatography was performed using a TSKgel Phenyl Toyopearl 650M (Tosoh Corporation), in which elution was performed with a 50 mM potassium phosphate buffer (pH 7.0) containing 1 mM DTT, under 1.5 to 0 M ammonium sulfate gradient. The resulting active fractions were dialyzed with a 50 mM potassium phosphate buffer (pH 7.0) containing 1 mM DTT, and supplemented with ammonium sulfate to 1.5 M. This was followed by column chromatography using 1 ml of RESOURCE ISO (AmershamPharmacia), in which elution was performed with a 50 mM potassium phosphate buffer (pH 7.0) containing 1 mM DTT, under 1.5 to 0 M ammonium sulfate gradient. The resulting active fractions were dialyzed with a 50 mM potassium phosphate buffer (pH 7.0) containing 1 mM DTT, and purified hydantoin racemase was obtained.

An analysis of the purified hydantoin racemase by SDS-polyacrylamide electrophoresis showed a substantially single band of hydantoin racemase. The purified hydantoin racemase was shown to have a purity of about 93% by HPLC analysis (column: YMC-Pack PROTEIN-RP (YMC Co., Ltd.), eluent: 20% acetonitrile aqueous solution to 80% acetonitrile aqueous solution gradient, flow rate: 1 ml/min., column temperature: 25° C., detection: 230 nm).

Example 2

Properties of Hydantoin Racemase

Properties of the purified hydantoin racemase obtained in Example 1 were examined as follows.

[N-Terminus Amino Acid Sequence]

Using the hydantoin racemase collected in the HPLC analysis of Example 1, analysis of N-terminus amino acid sequence was performed with a protein sequencer Procise 492 (Applied Biosystems Ltd.). As a result, the sequence of 40 amino acids at the N-terminus was determined. The sequence is represented by SEQ ID NO: 3 of the Sequence Listing.

[Relative Activity]

The activity of the purified hydantoin racemase was determined by HPLC, by quantifying the amount of increase of D-5-(2-methylthioethyl)hydantoin generated at 30° C. in 30 minutes in a 50 mM Tris-HCl buffer (pH 7.5) containing 50 mM L-5-(2-methylthioethyl)hydantoin. HPLC analysis was performed under the following conditions. Column: Chirobiotic T (4.6 mm×250 mm, ASTEC Inc.), eluent: 0.01% (v/v) triethylamine acetate (pH 6.8)/methanol=9/1, flow rate: 0.7 ml/min., column temperature: 35° C., detection: 210 nm. Here, 1 unit was defined as the amount of enzyme that generated 1 μmol D-5-(2-methylthioethyl)hydantoin in one minute. Quantification of protein was performed according to the Lowry method, using BSA as a standard. The result showed that the purified hydantoin racemase had a relative activity of 24.2 unit/mg protein.

[Measurement of Km Value]

Figure 2:
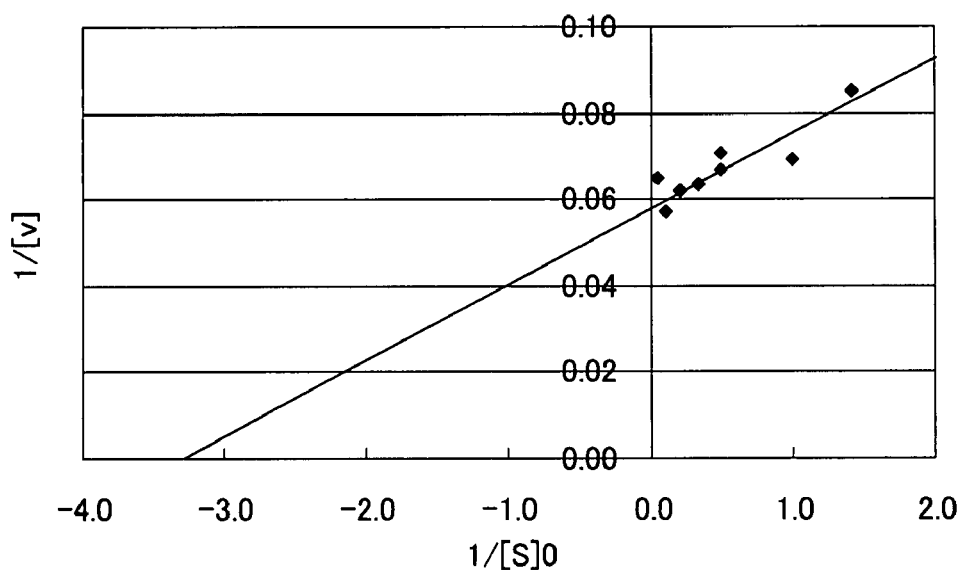
FIG. 2 is a graph representing Km values for L-5-(2-methylthioethyl)hydantoin of hydantoin racemase according to an embodiment of the present invention.

A Km value for L-5-(2-methylthioethyl)hydantoin was determined from the Lineweaver-Burk plot. As shown in FIG. 2, the Km value for L-5-(2-methylthioethyl)hydantoin was 0.304 mM.

[Effective Temperature Range and Optimum Temperature]

Figure 3:
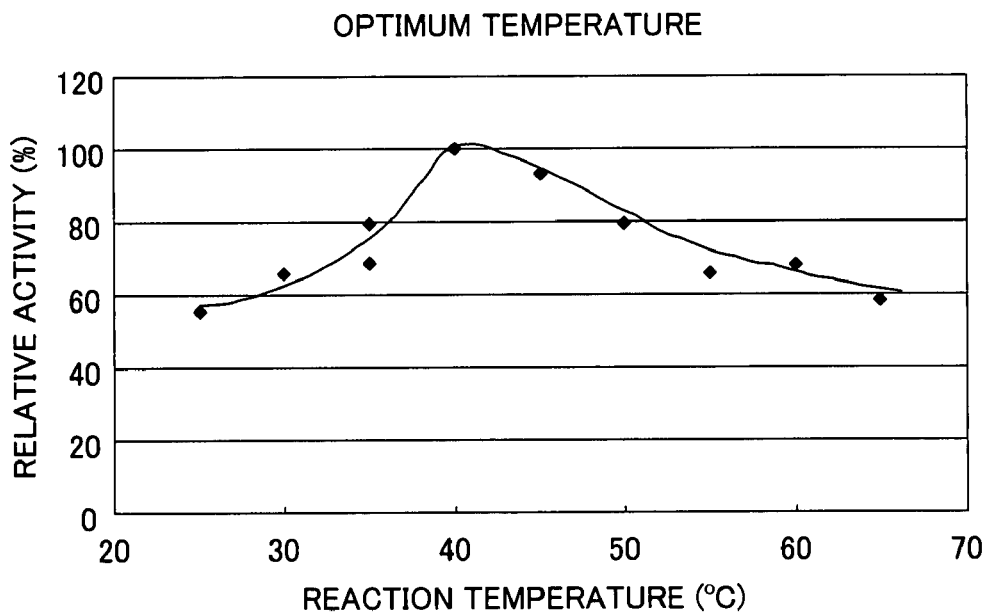
FIG. 3 is a graph representing an effective temperature range and optimum temperature of hydantoin racemase according to an embodiment of the present invention.

Assessment was made as to effective temperature range and optimum temperature. FIG. 3 represents relative activities at different temperatures, taking the activity at 40° C. at 100%. The optimum temperature of the enzyme was 40° C., and the enzyme desirably exerted its action at all temperatures in the evaluated temperature range of 25° C. to 65° C.

[Effective pH Range]

Figure 4:
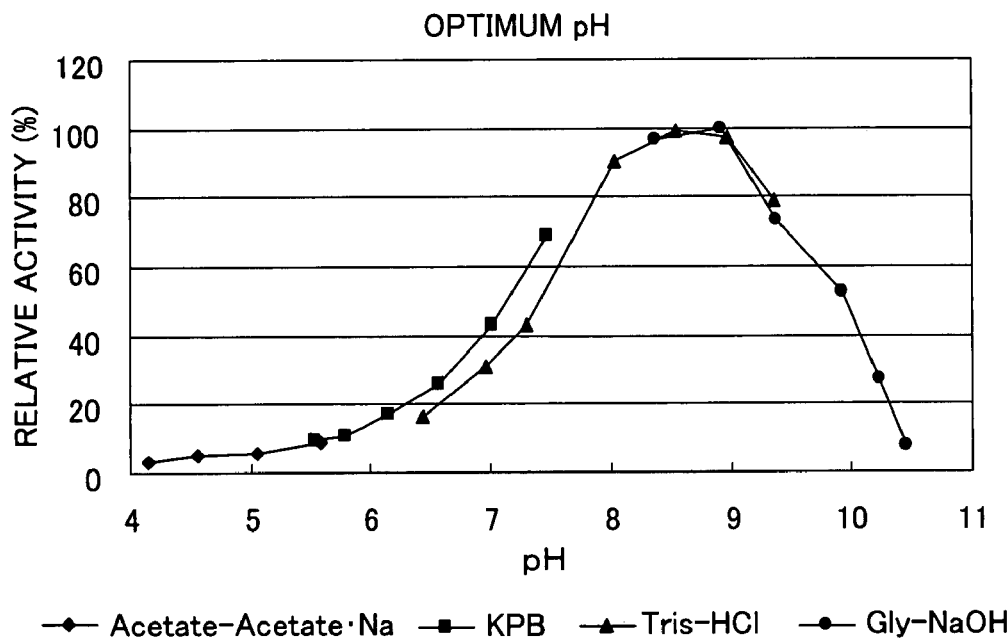
FIG. 4 is a graph representing an effective pH range and optimum pH of hydantoin racemase according to an embodiment of the present invention.

Assessment was made as to effective pH range and optimum pH. FIG. 4 shows relative activities at different pH, taking the activity at pH 8.9 at 100%. The enzyme exerted its action in a pH range of 6 to 10. The optimum pH range was 8 to 9.

[Temperature Stability]

Figure 5:
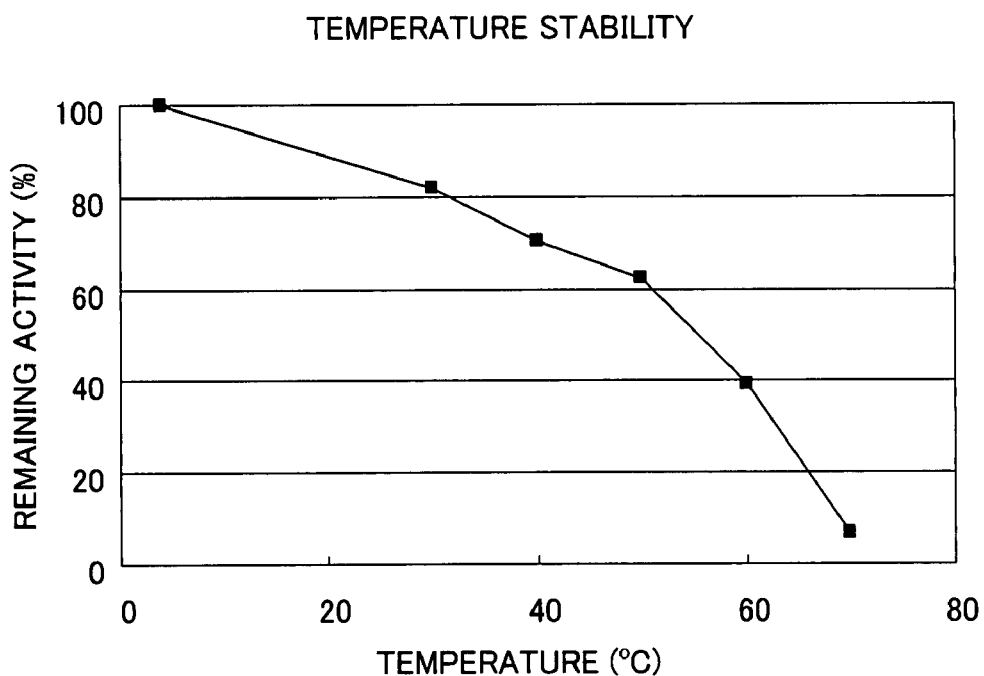
FIG. 5 is a graph representing temperature stability of hydantoin racemase according to an embodiment of the present invention.

Temperature stability of enzyme was examined as the remaining activity after 30 minutes of processing at different temperatures. As shown in FIG. 5, the remaining activity was 80% at 30° C. At 70° C., almost all activity was lost.

Figure 6:
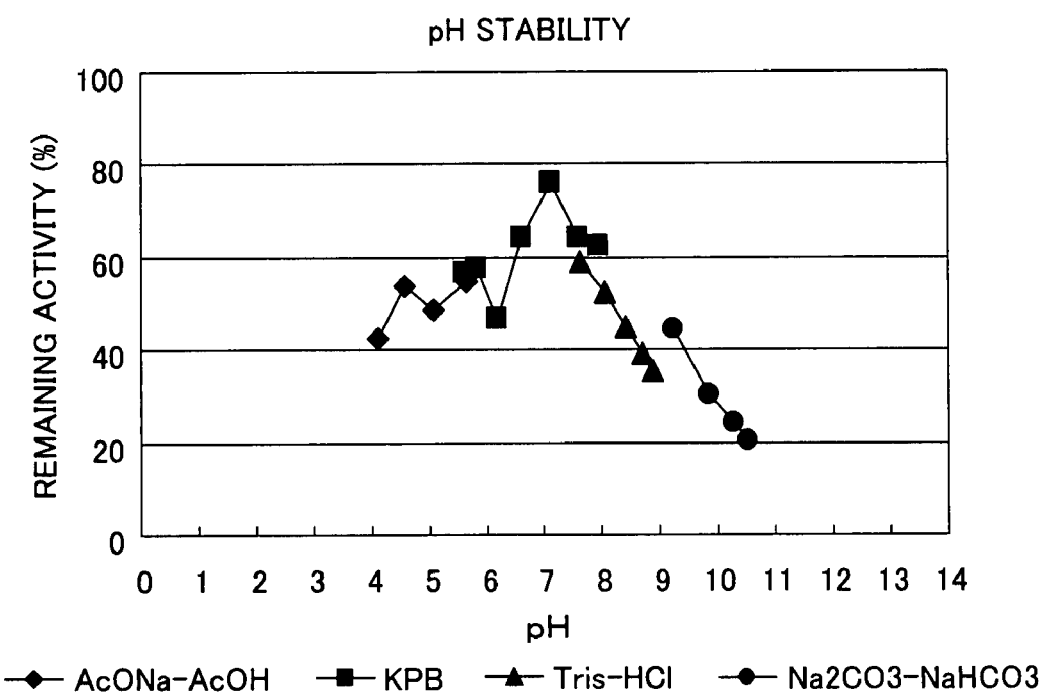
FIG. 6 is a graph representing pH stability of hydantoin racemase according to an embodiment of the present invention.

[pH Stability]

pH stability was examined. FIG. 6 represents remaining activity of enzyme after processing the enzyme at 30° C. for 16 hours at different pH, taking the activity of untreated enzyme at 100%. The enzyme was relatively stable in a pH range of 4.5 to 8.0.

[Measurement of Molecular Weight]

Measurement of molecular weight was performed based on comparison with the elution time of the standard protein, using gel filtration chromatography (column: TSKgel G3000SW (Tosoh Corporation). The molecular weight was found to be about 139,000. Measurement of subunit molecular weight was also measured based on comparison with the mobility of the standard protein, using SDS-polyacrylamide electrophoresis. The molecular weight of subunit was found to be about 31,000.

[Substrate Specificity]

Substrate specificity of purified hydantoin racemase was examined. First, 0.1 ml of purified hydantoin racemase obtained in Example 1 was added to each 0.9 ml of 50 mM Tris-HCl buffers (pH 7.5) containing 50 mM L-5-(2-methylthioethyl)hydantoin, 50 mM D-5-(2-methylthioethyl)hydantoin, 13 mM D-5-(1-mercapto-1-methyl)ethylhydantoin, 8 mM L-5-isobutylhydantoin, 50 mM L-5-(1-methylpropyl)hydantoin, and 4 mM L-5-benzylhydantoin, respectively. The mixtures were allowed to react at 30° C., and the reaction was terminated by adding 0.1 ml of 1N HCl. Except for the reaction using the substrate D-5-(1-mercapto-1-methyl)ethylhydantoin, the reaction was analyzed by diluting the supernatant of a centrifuged reaction mixture two times with ion exchange water, and by quantifying the D-5-substituted hydantoin compound generated in the reaction mixture, using HPLC. HPLC analysis was performed under the conditions given above. For the reaction using the substrate D-5-(1-mercapto-1-methyl)ethylhydantoin, the reaction mixture was analyzed by quantifying a sample that had been obtained by extracting the reaction mixture with 1 ml of ethyl acetate. Analysis was performed by performing HPLC under the following conditions. Column: CHIRALPAK AD-H (Daicel), eluent: hexane/isopropanol=9/1, flow rate: 1 ml/min., column temperature: 25° C., detection: 210 nm. Table 2 shows the result as relative activities, taking the activity for L-5-(2-methylthioethyl)hydantoin at 100.

TABLE 2

| Substrate | Relative Activity |
| --- | --- |
| L-5-(2-methylthioethyl)hydantoin | 100 |
| D-5-(2-methylthioethyl)hydantoin | 49 |
| D-5-(1-mercapto-1-methyl)ethylhydantoin | 25 |
| L-5-isobutylhydantoin | 173 |
| L-5-(1-methylpropyl)hydantoin | 2 |
| L-5-benzylhydantoin | 52 |

Example 3

Substrate Specificity of Hydantoin Racemase Produced by *Bacillus* sp. KNK519HR

Substrate specificity of hydantoin racemase produced by *Bacillus* sp. KNK519HR was examined using a crude enzyme solution of *Bacillus* sp. KNK519HR that was produced according to the procedure described in Example 1. First, 0.1 ml of crude enzyme solution was added to each 0.9 ml of 50 mM Tris-HCl buffers (pH 7.5) containing 4 mM L-5-benzylhydantoin, 50 mM L-5-(2-methylthioethyl)hydantoin, and 8 mM L-5-isobutylhydantoin, respectively. The mixtures were allowed to react at 30° C., and the reaction was terminated by adding 0.1 ml of 1N HCl. The supernatant of a centrifuged reaction mixture was diluted two times with ion exchange water, and the D-5-substituted hydantoin compound generated in the reaction mixture was quantified by HPLC. HPLC analysis was performed under the following conditions. Column: Chirobiotic T (4.6 mm×250 mm, ASTEC Inc., eluent: 0.01% (v/v) Triethylamine acetate (pH 6.8)/methanol=9/1, flow rate: 0.7 ml/min., column temperature: 35° C., detection: 210 nm. Further, 0.1 ml of crude enzyme solution of *Bacillus* sp. KNK519HR was added to 0.9 ml of 50 mM Tris-HCl buffer (pH 7.5) containing 50 mM 5-methylhydantoin, together with recombinant *Escherichia coli* having D-form selective hydantoinase activity for 1 ml of culture solution (described later), and recombinant *Escherichia coli* having D-form selective N-carbamylamino acid amidohydrolase activity for 1 ml of culture solution. The mixture was allowed to react at 30° C., and the reaction was terminated by adding 0.1 ml of 1N HCl. After neutralization with 1N NaOH, the reaction mixture was centrifuged and the D-alanine generated in the supernatant was quantified by an enzyme method using D-amino acid oxydase and peroxydase.

Quantification of D-alanine by the enzyme method was performed as follows. The supernatant of reaction mixture was diluted 5 times with ion exchange water, and was mixed at a 1:1 ratio with a color reagent containing 1.3 mM 4-aminoantipyrin, 2.2 mM N-ethyl-N-(2-hydroxy-3-sulfopropyl)-m-toluidine, 0.8 U/ml peroxydase (CALZYME Laboratories, Inc., Product Number 100A0600), 1.2 U/ml of D-amino acid oxydase (SIGMA, Product Number A5222), and 40 mM potassium phosphate buffer (pH 7.9). The mixture was allowed to react for 90 minutes, and an absorbance at 555 nm was measured to quantity the D-alanine generated in the reaction mixture. The result is shown in Table 3 as relative activities, taking the activity for L-5-isobutylhydantoin at 100.

As the culture solutions used in this Example, the culture solution of recombinant *Escherichia coli* having D-form selective hydantoinase activity, and the culture solution of recombinant *Escherichia coli* having D-form selective N-carbamylamino acid amidohydrolase activity were obtained as follows. *Escherichia coli* HB101 (pTH104) (FERM BP-4864) as the recombinant *Escherichia coli* having D-form selective hydantoinase activity was inoculated in a 50-ml medium (16 g tryptone, 10 g yeast extract, 5 g sodium chloride, 1 l water, 400 ppm manganese chloride, pH 7 prior to sterilization, 100 ppm ampicillin sodium separately sterilized by filtration) that had been sterilized in a 500-ml Sakaguchi flask. The cells were cultured at 37° C. for 24 hours with shaking. *Escherichia coli* HB101 (pNT4553) (FERM BP-4368) as the recombinant *Escherichia coli* having D-form selective N-carbamylamino acid amidohydrolase activity was inoculated in a 350-ml medium (16 g tryptone, 10 g yeast extract, 5 g sodium chloride, 1 l water, pH 7 prior to sterilization, 100 ppm ampicillin sodium separately sterilized by filtration) that had been sterilized in a 500-ml Sakaguchi flask. The cells were cultured at 37° C. for 36 hours with shaking.

TABLE 3

| Substrate | Relative Activity |
| --- | --- |
| L-5-isobutylhydantoin | 100 |
| L-5-(2-methylthioethyl)hydantoin | 61 |
| L-5-benzylhydantoin | 35 |
| L-5-methylhydantoin | 20 |

*Escherichia coli* HB101 (pTH104) (FERM BP-4864) was deposited on Nov. 2, 1994, and *Escherichia coli* HB101 (pNT4553) (FERM BP-4368) was deposited on Jul. 22, 1993, at the International Patent Organism Depository (IPOD), the National Institute of Advanced Industrial Science and Technology, whose address is Tsukuba Central 6, 1-1-1 Higashi, Tsukuba, Ibaraki, Japan, 305-8566.

Example 4

Substrate Inhibition of Hydantoin Racemase Produced by *Bacillus* sp. KNK519HR

Figure 7:
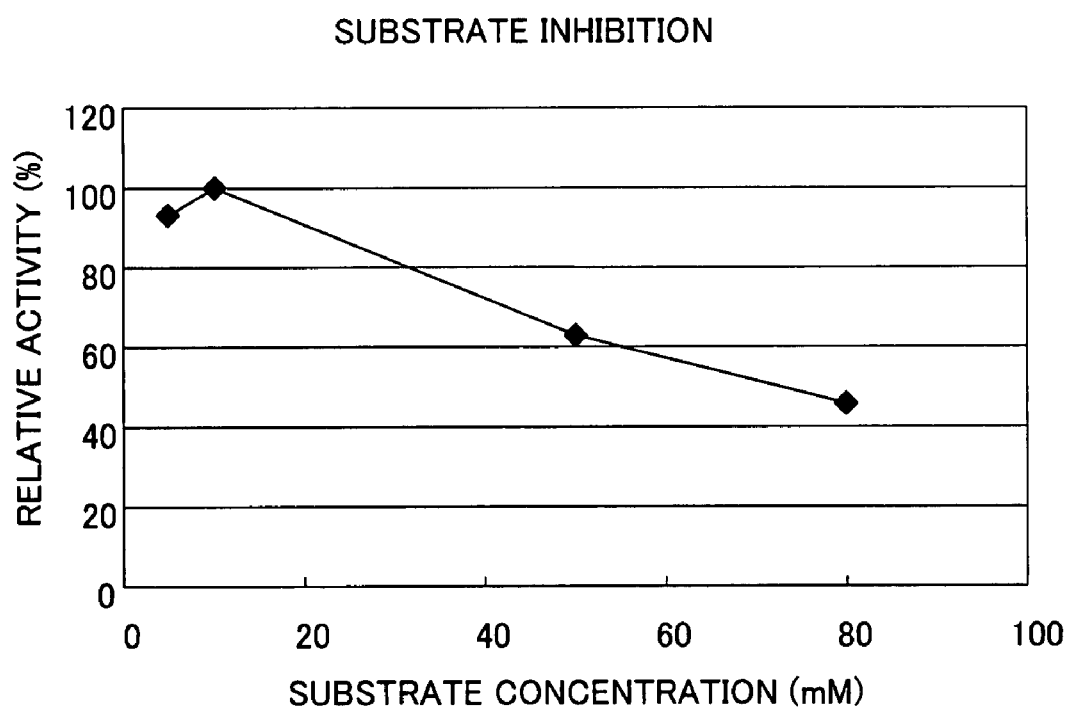
FIG. 7 is a graph representing effect of substrate inhibition of hydantoin racemase according to an embodiment of the present invention.

Substrate inhibition of the hydantoin racemase produced by *Bacillus* sp. KNK519HR was examined using the crude enzyme solution prepared in Example 1. In a reaction mixture of 0.1-ml crude enzyme solution and each 0.9-ml of 50 mM Tris-HCl buffers (pH 7.5) respectively containing 5, 10, 50, and 80 mM L-5-(2-methylthioethyl)hydantoin, respectively, the reaction was performed at 30° C. for 10, 20, 30, and 40 minutes. After the reaction, hydantoin racemase activity was abolished by adding 0.1 ml of 1N HCl. The supernatant of the centrifuged reaction mixture was diluted two times with ion exchange water, and the D-5-(2-methylthioethyl)hydantoin generated in the reaction mixture was quantified by HPLC. HPLC analysis was performed under the same conditions used in Example 3. An initial reaction rate was determined at each initial substrate concentration. FIG. 7 represents a relationship between relative activity and initial substrate concentration. The result showed that the hydantoin racemase produced by *Bacillus* sp. KNK519HR had substrate inhibition when L-5-(2-methylthioethyl)hydantoin was used as the substrate between 50 mM and 80 mM.

Example 5

Isolation of Hydantoin Racemase Gene

Colonies of *Bacillus* sp. KNK519HR were inoculated in a 10-ml medium (16 g tryptone peptone (DIFCO), 10 g bacto yeast extract (Becton Dickinson and Company), 5 g NaCl, adjusted to 1 liter by adding water and to pH 7, sterilized with an autoclave prior to use). The cells were aerobically cultured at 30° C. for 12 hours with shaking.

After culturing, the cells were collected by centrifugation, and a DNA solution was obtained using a UltraClean Microbial DNA Isolation Kit (MO BIO Laboratories, Inc.). The DNA solution was then deposited with ethanol, and the sediment obtained by centrifugation was dissolved in 10 mM Tris-HCl buffer (pH 8.0, 1 mM ethylenediaminetetraacetic acid) to prepare chromosomal DNA. Using the chromosomal DNA as a template, PCR was performed with a DNA primer (Primer-1: SEQ ID NO: 4 of the Sequence Listing) that had been designed based on the N-terminus amino acid sequence obtained in Example 2, and a DNA primer (Primer-2: SEQ ID NO: 5 of the Sequence Listing) that had been designed based on a complementary sequence portion of known hydantoin racemase. As a result, part of target hydantoin racemase gene (referred to as "partial gene") was obtained.

In order to obtain a full-length target gene, the following procedure was performed. Based on the base sequences of the partial gene respectively corresponding to the N- and C-terminus sequences of the enzyme, DNA primers facing outward from the partial gene (Primer-3: SEQ ID NO: 6 of the Sequence Listing, Primer-4: SEQ ID NO: 7 of the Sequence Listing) were synthesized. Inverse PCR was performed using these primers. As the template, a cyclic DNA that had been obtained by digesting the chromosomal DNA with restriction enzymes KpnI and SpeI and ligating fragments of the chromosomal DNA with T4 DNA ligase was used. As a result, DNA fragments were obtained that contained partial genes facing outward of the previously obtained partial gene. After determining base sequences of the DNA fragments, PCR was performed to obtain a DNA fragment (SEQ ID NO: 10 of the Sequence Listing) that contained a full-length hydantoin racemase gene. This was performed by amplifying DNA between sequences of a DNA primer (Primer-5: SEQ ID NO: 8 of the Sequence Listing) that had been ligated to the cutting site of restriction enzyme NdeI in a portion that was assumed to lie upstream of the enzyme N-terminus, and a DNA primer (Primer-6: SEQ ID NO: 9 of the Sequence Listing) that had been ligated to the cutting site of restriction enzyme EcoRI in a portion that was assumed to lie downstream of the C-terminus, using the chromosomal DNA as the template. A base sequence analysis revealed that the resulting DNA fragment had a full-length hydantoin racemase gene (SEQ ID NO: 2 of the Sequence Listing).

Example 6

Construction of Recombinant Plasmid Expressing Hydantoin Racemase Gene

A DNA fragment with the open reading frame represented by SEQ ID NO: 2 of the Sequence Listing was obtained by performing PCR, using the chromosomal DNA of Example 5 as the template. This was performed by amplifying DNA between sequences of primers (Primer-7: SEQ ID NO: 11 of the Sequence Listing, Primer-8: SEQ ID NO: 12 of the Sequence Listing) that had been respectively ligated to the cutting sites of restriction enzymes NdeI and EcoRI in the N- and C-terminus portions of the hydantoin racemase gene obtained in Example 5.

The DNA fragment was excised with restriction enzymes NdeI and EcoRI and ligated with T4 DNA ligase to a vector plasmid pUCNT (see International Publication WO94/03613) that had been excised with the same restriction enzymes. As a result, pBHR001 was obtained that is designed to produce the hydantoin racemase gene in a large quantity, as shown in the restriction map of FIG. 1.

Example 7

Construction of Transformant Using Recombinant DNA Including Hydantoin Racemase Gene The plasmid pBHR001 obtained in Example 6 was combined with competent cells of *Escherichia coli* HB101 to perform transformation. The transformed cells were plated on agar medium (10 g tryptone, 5 g yeast extract, 10 g sodium chloride, 15 g agar, 100 mg ampicillin, adjusted to 1 liter with deionized water, pH 7.0 prior to sterilization, ampicillin being added after sterilization) to obtain colonies of transformed *Escherichia coli* HB101 (pBHR001) including recombinant DNA with hydantoin racemase gene.

The colonies of transformant so obtained were inoculated in a 6-ml medium (the foregoing medium without agar) that had been sterilized in a test tube. The cells were aerobically cultured at 37° C. for 23 hours with shaking. The cells were collected from the culture solution by centrifugation, and suspended in a 50 mM Tris-HCl buffer (pH 7.5). After sonicating the cells, insoluble components originating in the cells were removed to obtain a hydantoin racemase enzyme solution of the transformant. Using 0.1 ml of the enzyme solution, hydantoin racemase activity was measured according to the method of Example 2. The result confirmed hydantoin racemase activity.

Example 8

Substrate Specificity of Hydantoin Racemase of Transformant

Using the hydantoin racemase enzyme solution of transformant obtained in Example 7, substrate specificity was examined according to the method of Example 2. The result is shown in Table 4 as relative activities, taking the activity for L-5-(2-methylthioethyl)hydantoin at 100.

TABLE 4

| Substrate | Relative Activity |
| --- | --- |
| L-5-(2-methylthioethyl)hydantoin | 100 |
| D-5-(2-methylthioethyl)hydantoin | 52 |
| D-5-(1-mercapto-1-methyl)ethylhydantoin | 9 |
| L-5-isobutylhydantoin | 174 |
| L-5-(1-methylpropyl)hydantoin | 2 |
| L-5-benzylhydantoin | 35 |

Example 9

Synthesis of Optically Active Amino Acid Using Bacteria with Hydantoin Racemase Activity In order to synthesize corresponding D-amino acids of DL-5-(2-methylthioethyl)hydantoin and DL-5-methylhydantoin, these substrate were allowed to react with *Escherichia coli* HB101 (pTH104) (FERM BP-4864) and *Escherichia coli* HB101 (pNT4553) (FERM BP-4368), which are recombinant *Escherichia coli* having D-form selective hydantoinase activity, and recombinant *Escherichia coli* having D-form selective N-carbamylamino acid amidohydrolase activity, respectively, described in Example 3, together with the culture solution of *Bacillus* sp. KNK519HR having hydantoin racemase activity cultured in Example 1.

1. Synthesis of D-methionine from DL-5-(2-methylthioethyl)hydantoin

First, 0.5 ml of 50 mM Tris-HCl buffer (pH 7.5) containing 2% (w/v) DL-5-(2-methylthioethyl)hydantoin was used to prepare a suspension of (i) cells obtained from 1 ml of the culture solution of *Bacillus* sp. KNK519HR obtained in Example 1, (ii) cells obtained from 1 ml of culture solution of recombinant *Escherichia coli* having D-form selective hydantoinase activity obtained in Example 3, and (iii) cells obtained from 1 ml of culture solution of recombinant *Escherichia coli* having D-form selective N-carbamylamino acid amidohydrolase activity obtained in Example 3. Reaction was performed at 30° C. After 19 hours, the reaction mixture was supplemented with 0.05 ml of 1N HCl to terminate the reaction, and the supernatant was diluted 50 times with ion exchange water and analyzed by HPLC. HPLC analysis was performed under the conditions of Example 3. As a result, D-methionine was generated at a molar ratio of 80%. Optical purity was 86.0% ee. In a sample not supplemented with cultured Strain KNK519HR, D-methionine was generated at a molar ratio of 39%, and 38 mol % of L-5-(2-methylthioethyl)hydantoin remained.

2. Synthesis of D-alanine from DL-5-methylhydantoin

First, 0.5 ml of 50 mM Tris-HCl buffer (pH 7.5) containing 2% (w/v) DL-5-methylhydantoin was used to prepare a suspension of (i) cells obtained from 1 ml of culture solution of *Bacillus* sp. KNK519HR obtained in Example 1, (ii) cells obtained from 1 ml of culture solution of recombinant *Escherichia coli* having D-form selective hydantoinase activity obtained in Example 3, and (iii) cells obtained from 1 ml of culture solution of recombinant *Escherichia coli* having D-form selective N-carbamylamino acid amidohydrolase activity obtained in Example 3. Reaction was performed at 30° C. After 18 hours, the reaction mixture was supplemented with 0.05 ml of 1N HCl to terminate the reaction, and then diluted 20 times with ion exchange water. Finally, the reaction mixture was centrifuged and the supernatant was analyzed by HPLC.

HPLC analysis was performed under the following conditions. Column: CROWNPAK CR+ (4.6 mm×150 mm, Daicel), eluent: $HClO_4$ (pH 1.5), flow rate: 0.4 ml/min., column temperature: 4° C., detection: 210 nm. The result showed an increase in the amount of D-alanine with the percent remain of 3.6% for DL-5-methylhydantoin, as compared with 32% in a sample not supplemented with the cultured Strain KNK519HR.

Example 10

Synthesis of Optically Active N-Carbamylamino Acid and Optically Active Amino Acid Using Transformants The culture solutions of transformants were centrifuged to collect therefrom (i) a transformant having hydantoin racemase activity obtained in Example 7, (ii) recombinant *Escherichia coli* (*Escherichia coli* HB101 (pTH104)) having D-form selective hydantoinase activity obtained in Example 3, and (iii) recombinant *Escherichia coli* (*Escherichia coli* HB101 (pNT4553)) having D-form selective N-carbamylamino acid amidohydrolase activity obtained in Example 3. The cells were suspended in 50 mM Tris-HCl buffer (pH 7.5) and sonicated to obtain enzyme solutions of the respective samples. The enzyme solutions were allowed to react with DL-5-isobutylhydantoin, DL-5-(2-methylthioethyl)hydantoin, DL-5-(1-mercapto-1-methyl)ethylhydantoin, or DL-5-benzylhydantoin to synthesize D-N-carbamylamino acid or D-amino acid corresponding to these substrates.

1. Synthesis of D-leucine from DL-5-isobutylhydantoin

First, 2 ml of 0.83 M 2-[4-(2-hydroxyethyl)-1-piperazinyl] ethanesulfonic acid (HEPES)-NaOH buffer (pH 7.0) containing 5% (w/v) DL-5-isobutylhydantoin was used to prepare a suspension of a disrupted cell solution of (i) 2 ml of culture solution of transformant having hydantoin racemase activity, (ii) 2 ml of culture solution of recombinant bacteria with D-form selective hydantoinase activity, and (iii) 10 ml of culture solution of recombinant bacteria with D-form selective N-carbamylamino acid amidohydrolase activity. Reaction was performed at 30° C. As a comparative example, the reaction was also performed without adding a disrupted cell solution of recombinant bacteria with hydantoin racemase activity. After 2 hours, the reaction mixture was diluted 50 times with 0.01% (v/v) triethylamine acetate (pH 6.8)/methanol=9/1, and the supernatant of centrifuged reaction mixture was analyzed by HPLC. As a result, 100% ee D-leucine was generated at the conversion rate of 99% (L-form n.d.). The conversion rate was 26% in the comparative example in which the reaction was performed without the disrupted cell solution of recombinant bacteria having hydantoin racemase activity. Quantification of amino acid by HPLC analysis was performed under the following conditions. Column: CROWNPAK CR+ (4.6 mm×150 mm, Daicel), eluent: $HClO_4$ (pH 1.5), flow rate: 1 ml/min., column temperature: 25° C., detection: 210 nm.

2. Synthesis of D-N-carbamylleucine from DL-5-isobutylhydantoin

First, 2 ml of 0.2 M Tris-HCl buffer (pH 8.5) containing 5% (w/v) DL-5-isobutylhydantoin was used to prepare a suspension of a disrupted cell solution of (i) cells obtained from 2 ml of culture solution of transformant having hydantoin racemase activity, and (ii) cells obtained from 2 ml of culture solution of recombinant bacteria having D-form selective hydantoinase activity. Reaction was performed at 30° C. As a comparative example, the reaction was also performed without adding a disrupted cell solution of recombinant bacteria having hydantoin racemase activity. After 6 hours, the reaction mixture was diluted 50 times with 0.01% (v/v) triethylamine acetate (pH 6.8)/methanol=9/1, and the supernatant of centrifuged reaction mixture was analyzed by HPLC. As a result, 100% ee D-N-carbamylleucine was generated at the conversion rate of 74% (L-form n.d.). The conversion rate was 49% in the comparative example in which the reaction was performed without the disrupted cell solution of recombinant bacteria having hydantoin racemase activity. Quantification by HPLC analysis was performed under the following conditions. Column: two pieces of Chirobiotic T (4.6 mm×250 mm, ASTEC Inc.) joined together, eluent: 0.01% (v/v) triethylamine acetate (pH 6.8)/methanol=9/1, flow rate: 0.7 ml/min., column temperature: 35° C., detection: 210 nm.

3. Synthesis of D-leucine from L-5-isobutylhydantoin

First, 2 ml of 0.63 M HEPES-NaOH buffer (pH 7.0) containing 5% (w/v) L-5-isobutylhydantoin was used to prepare a suspension of a disrupted cell solution of (i) cells obtained from 2 ml of culture solution of transformant having hydantoin racemase activity, and (ii) cells obtained from 2 ml of culture solution of recombinant bacteria having D-form selective hydantoinase activity, and (iii) cells obtained from 8 ml of culture solution of recombinant bacteria having D-form selective N-carbamylamino acid amidohydrolase activity. Reaction was performed at 40° C. After 2.5 hours, the reaction mixture was diluted 50 times with 10 mM potassium phosphate buffer (pH 2.0)/acetonitrile=95/5, and the supernatant of centrifuged reaction mixture was analyzed by HPLC. As a result, 100% ee D-leucine was generated at the conversion rate of 99% (L-form n.d.). Quantification of amino acid by HPLC analysis was performed under the same conditions given in Section 1 above.

4. Synthesis of D-methionine from DL-5-(2-methylthioethyl)hydantoin

First, 2 ml of 100 mM potassium phosphate buffer (pH 7.0) containing 1% (w/v) DL-5-(2-methylthioethyl)hydantoin was used to prepare a suspension of a disrupted cell solution of (i) cells obtained from 2 ml of culture solution of recombinant bacteria having hydantoin racemase activity, (ii) cells obtained from 2 ml of culture solution of recombinant bacteria having D-form selective hydantoinase activity, and (iii) cells obtained from 2 ml of culture solution of recombinant bacteria having D-form selective N-carbamylamino acid amidohydrolase activity. Reaction was performed at 40° C. As a comparative example, the reaction was also performed without adding a disrupted cell solution of recombinant bacteria having hydantoin racemase activity. After 2 hours, the reaction mixture was diluted 20 times with 10 mM potassium phosphate buffer (pH 2.0)/acetonitrile=95/5, and the supernatant of centrifuged reaction mixture was analyzed by HPLC. As a result, D-methionine was generated at the conversion rate of 93%. The conversion rate was 47% in the comparative example in which the reaction was performed without adding the disrupted cell solution of recombinant bacteria having hydantoin racemase activity. Quantification of amino acid by HPLC was performed under the following conditions. Column: Develosil ODS HG-5 (4.6 mm×150 mm, Nomura Chemical Co., Ltd.), eluent: 60 mM potassium phosphate buffer (5 mM sodium decanesulfonate)/methanol=3/1, flow rate: 1 ml/min., column temperature: 40° C., detection: 210 nm.

5. Synthesis of D-penicillamine from DL-5-(1-mercapto-1-methyl)ethylhydantoin

First, 2 ml of 100 mM HEPES-NaOH buffer (pH 7.0) containing 1% (w/v) DL-5-(1-mercapto-1-methyl)ethylhydantoin was used to prepare a suspension of a disrupted cell solution of (i) cells obtained from 2 ml of culture solution of recombinant bacteria having hydantoin racemase activity, (ii) cells obtained from 2 ml of culture solution of recombinant bacteria having D-form selective hydantoinase activity, and (iii) cells obtained from 4 ml of culture solution of recombinant bacteria having D-form selective N-carbamylamino acid amidohydrolase activity. Reaction was performed at 40° C. As a comparative example, the reaction was also performed without adding a disrupted cell solution of recombinant bacteria having hydantoin racemase activity. After 2.5 hours, the reaction mixture was diluted 20 times with 10 mM potassium phosphate buffer (pH 2.0)/acetonitrile=95/5, and the supernatant of centrifuged reaction mixture was analyzed by HPLC. As a result, 100% ee D-penicillamine was generated at the conversion rate of 86% (L-form n.d.). The conversion rate was 52% in the comparative example in which the reaction was performed without adding the disrupted cell solution of recombinant bacteria having hydantoin racemase activity. HPLC analysis was performed under the same conditions given in Section 4 above.

6. Synthesis of D-phenylalanine from DL-5-benzylhydantoin

The reaction was performed under the same conditions described in Section 1 except that DL-5-benzylhydantoin was used as the substrate. As a comparative example, the reaction was also performed without adding the disrupted cell solution of recombinant bacteria having hydantoin racemase activity. After 9 hours of reaction, 98.1% ee D-phenylalanine was generated at the conversion rate of 83%. The conversion rate was 40% in the comparative example in which the reaction was performed without adding the disrupted cell solution of recombinant bacteria having hydantoin racemase activity.

7. Synthesis of D-N-carbamylphenylalanine from DL-5-benzylhydantoin

The reaction was performed under the same conditions described in Section 2 except that DL-5-benzylhydantoin was used as the substrate. As a comparative example, the reaction was also performed without adding the disrupted cell solution of recombinant bacteria having hydantoin racemase activity. After 20 hours of reaction, D-N-carbamylphenylalanine was generated at the conversion rate of 84%. The conversion rate was 48% in the comparative example in which the reaction was performed without adding the disrupted cell solution of recombinant bacteria having hydantoin racemase activity.

The invention claimed is:

1. An isolated polypeptide comprising the amino acid sequence of SEQ ID NO: 1.

2. An isolated DNA encoding a polypeptide having hydantoin racemase activity,
   said DNA selected from the group consisting of: (1) a DNA that encodes a polypeptide comprising the amino acid sequence of SEQ ID NO: 1; (2) a DNA consisting of the polynucleotide sequence of SEQ ID NO: 2; and (3) a DNA consisting of the polynucleotide sequence of SEQ ID NO: 2 in which 1 to 8 bases are substituted, deleted, inserted and/or added.

3. An isolated polypeptide encoded by a DNA selected from the group consisting of: a DNA consisting of the polynucleotide sequence of SEQ ID NO: 2 and; a DNA consisting of the polynucleotide sequence of SEQ ID NO: 2 in which 1 to 8 bases are substituted, deleted, inserted and/or added.

4. A recombinant plasmid comprising the DNA of claim 2.

5. The recombinant plasmid of claim 4, wherein said recombinant plasmid is a plasmid pBHR001 separatable from *Escherichia coli* HB101 (pBHR001) (FERM BP-10476).

6. A transformant obtained by transforming a host microorganism with the recombinant plasmid of claim 4.

7. The transformant of claim 6, wherein the host microorganism is *Escherichia coli*.

8. The transformant of claim 7, wherein the transformant is *Escherichia coli* HB101 (pBHR001) (FERM BP-10476).

9. An isolated microorganism that produces the polypeptide of claim 1, wherein said microorganism belongs to the Genus *Bacillus*.

10. The isolated microorganism of claim 9, wherein the microorganism is *Bacillus* sp. KNK519HR (FERM BP-10477), or a mutant strain thereof.

11. A process for producing hydantoin racemase, comprising culturing the transformant of claim 6, accumulating a polypeptide having hydantoin racemase activity in a culture of the transformant, and collecting the polypeptide.

12. A process for producing hydantoin racemase, comprising culturing the microorganism of claim 9, accumulating said polypeptide in a culture of the microorganism, and collecting the polypeptide.

13. A process for racemizing optically active 5-substituted hydantoin, comprising causing an optically active 5-substituted hydantoin compound to be acted upon by a polypeptide of claim 1.

14. A process for racemizing optically active 5-substituted hydantoin as set forth in claim 13, wherein the optically active 5-substituted hydantoin compound is optically active 5-substituted hydantoin represented by General Formula (1)

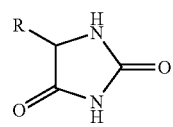

(1)

where R represents an alkyl group having 1 to 20 carbon atoms with or without a substituent, an aralkyl group having 7 to 20 carbon atoms with or without a substituent, or an aryl group having 6 to 20 carbon atoms with or without a substituent.

15. A process for producing optically active N-carbamylamino acid, comprising causing a 5-substituted hydantoin compound to be acted upon by a polypeptide of claim 1.

16. A process for producing optically active N-carbamylamino acid as set forth in claim 15,
wherein the optically active 5-substituted hydantoin compound is 5-substituted hydantoin represented by General Formula (1)

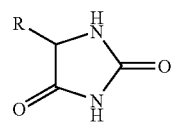

(1)

where R represents an alkyl group having 1 to 20 carbon atoms with or without a substituent, an aralkyl group having 7 to 20 carbon atoms with or without a substituent, or an aryl group having 6 to 20 carbon atoms with or without a substituent, and
wherein the optically active N-carbamylamino acid is optically active N-carbamylamino acid represented by General Formula (2)

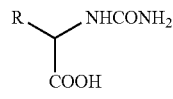

(2)

where R represents an alkyl group having 1 to 20 carbon atoms with or without a substituent, an aralkyl group having 7 to 20 carbon atoms with or without a substituent, or an aryl group having 6 to 20 carbon atoms with or without a substituent.

17. A process as set forth in claim 16, wherein the optically active N-carbamylamino acid is one of N-carbamyl-D-leucine, N-carbamyl-D-isoleucine, N-carbamyl-D-valine, N-carbamyl-D-norleucine, N-carbamyl-D-norvaline, N-carbamyl-D-methionine, N-carbamyl-D-cysteine, N-carbamyl-D-penicillamine, N-carbamyl-D-phenylalanine, N-carbamyl-D-phenylglycine, and N-carbamyl-D-4-hydroxyphenylglycine.

18. A process for producing an optically active amino acid, comprising causing a 5-substituted hydantoin compound to be acted upon by hydantoinase and N-carbamylamino acid amidohydrolase, together with the polypeptide of claim 1.

19. A process for producing an optically active amino acid as set forth in claim 18,
wherein the 5-substituted hydantoin compound is 5-substituted hydantoin represented by General Formula (1)

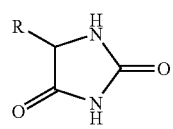

(1)

where R represents an alkyl group having 1 to 20 carbon atoms with or without a substituent, an aralkyl group having 7 to 20 carbon atoms with or without a substituent, or an aryl group having 6 to 20 carbon atoms with or without a substituent, and
wherein the optically active amino acid is represented by General Formula (3)

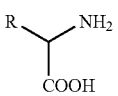

(3)

where R represents an alkyl group having 1 to 20 carbon atoms with or without a substituent, an aralkyl group having 7 to 20 carbon atoms with or without a substituent, or an aryl group having 6 to 20 carbon atoms with or without a substituent.

20. A process as set forth in claim 19, wherein the optically active amino acid is one of D-leucine, D-isoleucine, D-valine, D-norleucine, D-norvaline, D-methionine, D-cysteine, D-penicillamine, D-phenylalanine, D-phenylglycine, and D-4-hydroxyphenylglycine.

* * * * *